(12) United States Patent
Itkowitz et al.

(10) Patent No.: US 9,155,592 B2
(45) Date of Patent: *Oct. 13, 2015

(54) VIRTUAL MEASUREMENT TOOL FOR MINIMALLY INVASIVE SURGERY

(75) Inventors: Brandon D. Itkowitz, Sunnyvale, CA (US); Tao Zhao, Sunnyvale, CA (US); Simon Dimaio, Sunnyvale, CA (US); Wenyi Zhao, Mountain View, CA (US); Christopher J. Hasser, Los Altos, CA (US); Myriam J. Curet, Los Altos, CA (US); Catherine J. Mohr, Mountain View, CA (US); Hubert Stein, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1520 days.

This patent is subject to a terminal disclaimer.

(21) Appl. No.: 12/485,545

(22) Filed: Jun. 16, 2009

(65) Prior Publication Data

US 2010/0318099 A1 Dec. 16, 2010

(51) Int. Cl.
*A61B 5/103* (2006.01)
*A61B 5/117* (2006.01)
(Continued)

(52) U.S. Cl.
CPC ............ *A61B 19/2203* (2013.01); *A61B 5/1072* (2013.01); *A61B 8/4209* (2013.01);
(Continued)

(58) Field of Classification Search
CPC ....................................................... A61B 5/00
USPC ............ 600/587; 606/130; 700/245, 250, 264
See application file for complete search history.

(56) References Cited

U.S. PATENT DOCUMENTS

| 4,219,842 A | 8/1980 | Miller |
| 4,603,231 A | 7/1986 | Reiffel et al. |

(Continued)

FOREIGN PATENT DOCUMENTS

| EP | 1168246 A2 | 1/2002 |
| JP | 2005118232 A | 5/2005 |

(Continued)

OTHER PUBLICATIONS

U.S. Appl. No. 12/415,377, filed Mar. 21, 2009; first named inventor: Tao Zhao.

(Continued)

*Primary Examiner* — Rene Towa
*Assistant Examiner* — May Abouelela

(57) ABSTRACT

Robotic and/or measurement devices, systems, and methods for telesurgical and other applications employ input devices operatively coupled to tools so as to allow a system user to manipulate tissues and other structures being measured. The system may make use of three dimensional position information from stereoscopic images. Two or more discrete points can be designated in three dimensions so as to provide a cumulative length along a straight or curving structure, an area measurement, a volume measurement, or the like. The discrete points may be identified by a single surgical tool or by distances separating two or more surgical tools, with the user optionally measuring a structure longer than a field of view of the stereoscopic image capture device by walking a pair of tools "hand-over-hand" along the structure. By allowing the system user to interact with the tissues while designating the tissue locations, and by employing imaging data to determine the measurements, the measurement accuracy and ease of measurement may be enhanced.

14 Claims, 16 Drawing Sheets

(51) Int. Cl.

| | | |
|---|---|---|
| *G06F 19/00* | (2011.01) | |
| *A61B 19/00* | (2006.01) | |
| *A61B 18/14* | (2006.01) | |
| *A61B 17/28* | (2006.01) | |
| *A61B 8/08* | (2006.01) | |
| *A61B 17/00* | (2006.01) | |
| *A61B 8/00* | (2006.01) | |
| *A61B 5/107* | (2006.01) | |

(52) U.S. Cl.
CPC .......... *A61B 8/483* (2013.01); *A61B 17/00234* (2013.01); *A61B 17/282* (2013.01); *A61B 18/1482* (2013.01); *A61B 19/56* (2013.01); *A61B 2017/00477* (2013.01); *A61B 2019/461* (2013.01); *A61B 2019/505* (2013.01)

(56) References Cited

U.S. PATENT DOCUMENTS

| | | |
|---|---|---|
| 4,614,366 A | 9/1986 | North et al. |
| 5,175,616 A | 12/1992 | Milgram et al. |
| 5,217,003 A | 6/1993 | Wilk |
| 5,428,192 A | 6/1995 | Chen et al. |
| 5,432,528 A | 7/1995 | Ritter |
| 5,457,754 A | 10/1995 | Han et al. |
| 5,468,921 A | 11/1995 | Blake et al. |
| 5,561,708 A | 10/1996 | Remillard |
| 5,577,991 A * | 11/1996 | Akui et al. .................. 600/111 |
| 5,579,057 A * | 11/1996 | Banker et al. ................ 348/589 |
| 5,583,536 A | 12/1996 | Cahill, III |
| 5,657,095 A * | 8/1997 | Yoshida et al. ............... 348/584 |
| 5,797,900 A | 8/1998 | Madhani et al. |
| 5,808,665 A * | 9/1998 | Green ............................. 348/65 |
| 5,836,869 A | 11/1998 | Kudo et al. |
| 5,839,441 A | 11/1998 | Steinberg |
| 5,855,583 A * | 1/1999 | Wang et al. ................... 606/139 |
| 5,950,629 A | 9/1999 | Taylor et al. |
| 5,987,349 A * | 11/1999 | Schulz .......................... 600/427 |
| 6,057,833 A | 5/2000 | Heidmann et al. |
| 6,097,994 A * | 8/2000 | Navab et al. .................. 700/245 |
| 6,108,458 A | 8/2000 | Hart |
| 6,122,541 A | 9/2000 | Cosman et al. |
| 6,139,490 A | 10/2000 | Breidenthal et al. |
| 6,159,016 A | 12/2000 | Lubell et al. |
| 6,201,984 B1 | 3/2001 | Funda et al. |
| 6,246,900 B1 | 6/2001 | Cosman et al. |
| 6,424,885 B1 * | 7/2002 | Niemeyer et al. ............. 700/245 |
| 6,434,416 B1 | 8/2002 | Mizoguchi et al. |
| 6,459,926 B1 * | 10/2002 | Nowlin et al. ................. 600/429 |
| 6,468,265 B1 | 10/2002 | Evans et al. |
| 6,470,236 B2 * | 10/2002 | Ohtsuki ......................... 700/247 |
| 6,484,049 B1 | 11/2002 | Seeley et al. |
| 6,490,475 B1 | 12/2002 | Seeley et al. |
| 6,493,608 B1 | 12/2002 | Niemeyer |
| 6,522,906 B1 | 2/2003 | Salisbury, Jr. et al. |
| 6,587,750 B2 * | 7/2003 | Gerbi et al. ................... 700/245 |
| 6,612,980 B2 | 9/2003 | Chen et al. |
| 6,659,939 B2 * | 12/2003 | Moll et al. .................... 600/102 |
| 6,678,090 B2 | 1/2004 | Spink |
| 6,714,839 B2 | 3/2004 | Salisbury, Jr. et al. |
| 6,714,841 B1 | 3/2004 | Wright et al. |
| 6,720,988 B1 | 4/2004 | Gere et al. |
| 6,731,988 B1 | 5/2004 | Green |
| 6,741,757 B1 | 5/2004 | Torr et al. |
| 6,791,601 B1 | 9/2004 | Chang et al. |
| 6,799,065 B1 | 9/2004 | Niemeyer |
| 6,817,972 B2 | 11/2004 | Snow |
| 6,837,883 B2 | 1/2005 | Moll et al. |
| 6,839,456 B2 | 1/2005 | Touzawa et al. |
| 6,856,324 B2 | 2/2005 | Sauer et al. |
| 6,856,826 B2 | 2/2005 | Seeley et al. |
| 6,856,827 B2 | 2/2005 | Seeley et al. |
| 6,864,886 B1 | 3/2005 | Cavallaro et al. |
| 6,866,671 B2 | 3/2005 | Tierney et al. |
| 6,949,106 B2 * | 9/2005 | Brock et al. .................. 606/130 |
| 6,980,210 B1 | 12/2005 | Weiglhofer et al. |
| 7,075,556 B1 | 7/2006 | Meier et al. |
| 7,155,315 B2 * | 12/2006 | Niemeyer et al. ............. 700/245 |
| 7,194,118 B1 | 3/2007 | Harris et al. |
| 7,277,120 B2 * | 10/2007 | Gere et al. ...................... 348/45 |
| 7,689,014 B2 | 3/2010 | Abovitz et al. |
| 7,907,166 B2 | 3/2011 | Lamprecht et al. |
| 8,184,880 B2 | 5/2012 | Zhao et al. |
| 8,218,727 B2 | 7/2012 | Baumgart et al. |
| 8,423,182 B2 * | 4/2013 | Robinson et al. ............. 700/245 |
| 8,639,000 B2 | 1/2014 | Zhao et al. |
| 8,830,224 B2 | 9/2014 | Zhao et al. |
| 2002/0012460 A1 * | 1/2002 | Kochi et al. .................. 382/154 |
| 2002/0058929 A1 | 5/2002 | Green |
| 2003/0151809 A1 | 8/2003 | Takahashi et al. |
| 2003/0158463 A1 * | 8/2003 | Julian et al. .................. 600/104 |
| 2003/0210812 A1 | 11/2003 | Khamene et al. |
| 2003/0216715 A1 * | 11/2003 | Moll et al. ........................ 606/1 |
| 2004/0002642 A1 | 1/2004 | Dekel et al. |
| 2004/0009459 A1 | 1/2004 | Anderson et al. |
| 2004/0022418 A1 | 2/2004 | Oota |
| 2004/0039485 A1 | 2/2004 | Niemeyer et al. |
| 2004/0052333 A1 | 3/2004 | Sayre et al. |
| 2004/0070615 A1 | 4/2004 | Ewing et al. |
| 2004/0240725 A1 | 12/2004 | Xu et al. |
| 2004/0263613 A1 | 12/2004 | Morita |
| 2005/0054910 A1 | 3/2005 | Tremblay et al. |
| 2005/0154288 A1 | 7/2005 | Wang et al. |
| 2005/0179702 A1 | 8/2005 | Tomlinson et al. |
| 2006/0013473 A1 | 1/2006 | Woodfill et al. |
| 2006/0058919 A1 | 3/2006 | Sommer |
| 2006/0087504 A1 | 4/2006 | Meier et al. |
| 2006/0142657 A1 | 6/2006 | Quaid et al. |
| 2006/0241414 A1 * | 10/2006 | Nowlin et al. ................ 600/431 |
| 2006/0258938 A1 | 11/2006 | Hoffman et al. .............. 600/424 |
| 2007/0021738 A1 * | 1/2007 | Hasser et al. ..................... 606/1 |
| 2007/0038080 A1 | 2/2007 | Salisbury, Jr. et al. |
| 2007/0078334 A1 | 4/2007 | Scully et al. |
| 2007/0138992 A1 | 6/2007 | Prisco et al. |
| 2007/0147707 A1 | 6/2007 | Coste-Maniere et al. |
| 2007/0156017 A1 * | 7/2007 | Lamprecht et al. ........... 600/102 |
| 2007/0161854 A1 | 7/2007 | Alamaro et al. |
| 2007/0167702 A1 * | 7/2007 | Hasser et al. ................. 600/407 |
| 2007/0183041 A1 | 8/2007 | McCloy et al. |
| 2007/0211927 A1 | 9/2007 | Groszmann et al. |
| 2007/0265527 A1 * | 11/2007 | Wohlgemuth ................. 600/424 |
| 2008/0004603 A1 * | 1/2008 | Larkin et al. ...................... 606/1 |
| 2008/0013809 A1 | 1/2008 | Zhu et al. |
| 2008/0027356 A1 | 1/2008 | Chen et al. |
| 2008/0033240 A1 * | 2/2008 | Hoffman et al. .............. 600/109 |
| 2008/0046122 A1 * | 2/2008 | Manzo et al. ................. 700/245 |
| 2008/0065109 A1 | 3/2008 | Larkin |
| 2008/0125794 A1 * | 5/2008 | Brock et al. .................. 606/130 |
| 2008/0177284 A1 * | 7/2008 | Lee et al. ...................... 606/130 |
| 2008/0234866 A1 | 9/2008 | Kishi et al. |
| 2008/0285724 A1 | 11/2008 | Dehler |
| 2009/0015004 A1 | 1/2009 | Long |
| 2009/0036902 A1 | 2/2009 | DiMaio et al. |
| 2009/0046146 A1 | 2/2009 | Hoyt |
| 2009/0069821 A1 * | 3/2009 | Farritor et al. ................ 606/130 |
| 2009/0088634 A1 * | 4/2009 | Zhao et al. .................... 600/427 |
| 2009/0088773 A1 * | 4/2009 | Zhao et al. .................... 606/130 |
| 2009/0088897 A1 * | 4/2009 | Zhao et al. .................... 700/250 |
| 2009/0171332 A1 | 7/2009 | Bonneau |
| 2009/0171371 A1 * | 7/2009 | Nixon et al. .................. 606/130 |
| 2009/0192523 A1 * | 7/2009 | Larkin et al. ................. 606/130 |
| 2009/0192524 A1 * | 7/2009 | Itkowitz et al. ............... 606/130 |
| 2009/0248036 A1 * | 10/2009 | Hoffman et al. .............. 606/130 |
| 2009/0248041 A1 * | 10/2009 | Williams et al. .............. 606/130 |
| 2009/0268010 A1 * | 10/2009 | Zhao et al. ...................... 348/45 |
| 2009/0268011 A1 * | 10/2009 | Scott et al. ...................... 348/45 |
| 2009/0268012 A1 * | 10/2009 | Scott et al. ...................... 348/45 |
| 2009/0268015 A1 * | 10/2009 | Scott et al. ...................... 348/51 |
| 2009/0270678 A1 * | 10/2009 | Scott et al. .................... 600/109 |
| 2009/0326553 A1 | 12/2009 | Mustufa et al. |
| 2010/0149183 A1 * | 6/2010 | Loewke et al. ................ 345/424 |
| 2010/0168763 A1 * | 7/2010 | Zhao et al. .................... 606/130 |
| 2010/0169815 A1 * | 7/2010 | Zhao et al. .................... 715/771 |

(56) References Cited

U.S. PATENT DOCUMENTS

| | | | |
|---|---|---|---|
| 2010/0204713 A1* | 8/2010 | Ruiz Morales | 606/130 |
| 2010/0228249 A1* | 9/2010 | Mohr et al. | 606/41 |
| 2011/0050852 A1 | 3/2011 | Lamprecht et al. | |

FOREIGN PATENT DOCUMENTS

| | | | |
|---|---|---|---|
| JP | 2007-181670 A | | 7/2007 |
| JP | 2008228967 A | | 10/2008 |
| JP | 2008245838 A | * | 10/2008 |
| JP | 2008245838 A | | 10/2008 |
| WO | WO-0129681 A1 | | 4/2001 |
| WO | WO0229723 A1 | | 4/2002 |
| WO | WO03045333 A2 | | 6/2003 |
| WO | WO-2004029786 A1 | | 4/2004 |
| WO | WO-200537093 A1 | | 4/2005 |
| WO | WO-2005102202 A1 | | 11/2005 |
| WO | WO-2005119505 A2 | | 12/2005 |
| WO | WO-2006124388 A1 | | 11/2006 |
| WO | WO-2006131373 A2 | | 12/2006 |
| WO | WO-2007120351 A2 | | 10/2007 |
| WO | WO2008079546 A2 | | 7/2008 |
| WO | WO2009025783 A1 | | 2/2009 |
| WO | WO2009045827 A2 | | 4/2009 |
| WO | WO-2009085616 A1 | | 7/2009 |
| WO | WO-2010147766 A1 | | 12/2010 |
| WO | WO 2007120351 A3 | * | 6/2011 |

OTHER PUBLICATIONS

U.S. Appl. No. 12/428,657, filed Apr. 23, 2009; ; first named inventor: Tao Zhao.

U.S. Appl. No. 12/428,691, filed Apr. 23, 2009; ; first named inventor: Tao Zhao.

U.S. Appl. No. 12/465,020, filed May 13, 2009; first named inventor: Wenyi Zhao.

U.S. Appl. No. 12/465,029, filed May 13, 2009; first named inventor: Wenyi Zhao.

U.S. Appl. No. 12/485,503, filed Jun. 16, 2009; first named inventor: Brandon D. Itkowitz.

U.S. Appl. No. 12/495,304, filed Jun. 30, 2009; first named inventor: Tao Zhao.

U.S. Appl. No. 61/203,975; filed Dec. 31, 2008; first named inventor: Tao Zhao.

U.S. Appl. No. 61/204,082, filed Dec. 31, 2008; first named inventor: Wenyi Zhao.

Fischler, M. et al., "Random sample consensus: a paradigm for model fitting with applications to image analysis and automated cartography," Communications of the ACM, vol. 24 , No. 6, Jun. 1981, pp. 381-395.

Kim Miriam et al., "Computer Assisted 3D Measurements for Micro-Surgery," Proceedings of the Human Factors and Ergonomics Society 41st Annual Meeting, 1997, pp. 787-791, Human Factors and Ergonomics Society.

Kosaka, Akio et al., "Augmented Reality System for Surgical Navigation Using Robust Target Vision," IEEE Conference on Computer Vision and Pattern Recognition, 2000, vol. 2, pp. 187-194.

Lowe, David G., "Distinctive Image Features from Scale-Invariant Keypoints," International Journal of Computer Vision, vol. 60, No. 2, Nov. 2004, pp. 91-110.

Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.

Taylor, Russell H., et al., "An overview of computer-integrated surgery at the IBM Thomas J. Watson Research Center," IBM J Research and Development, 1996, pp. 163-183, vol. 40, Issue 2, IBM Corp.

Vertut, Jean and Phillipe Coiffet, "Robot Technology: Teleoperation and Robotics Evolution and Development—vol. 3A", English translation Prentice-Hall, Inc., Inglewood Cliffs, NJ, USA 1986, vol. 3A, 332 pages.

PCT/US10/37293 International Search Report and Written Opinion of the International Searching Authority, mailed Nov. 29, 2010, 19 pages.

Anderson B.L., "Stereovision: Beyond Disparity Computation," Trends in Cognitive Sciences, 1998, vol. 2 (6), pp. 214-222.

Ayala, Hugo M, et al., "Wear of Oil Containment Elastomer in Abrasive Slurries," 1998, pp. 9-21 , vol. 220—Issue. 1, Elsevier Science.

Barron, J.L. et al., "Performance of optical flow techniques," Intl. J. of Computer Vision, 1994, pp. 43-77, vol. 12—Issue. 1.

Benson, K. Blair, "Television Engineering Handbook," 1986, pp. 14.68-14.72, McGraw-Hill.

Boeckeler Instruments, Inc., "Pointmaker PVI-44 Compact Video Marker Manual," Section One, 2006, pp. 3-32.

Boeckeler Instruments, Inc., "Pointmaker PVI-X90 Presentation System," specification sheet, www.pointmaker.com, © 1994-2004, 2 pages.

Brown, Myron M. et al., "Advances in Computational Stereo," IEEE Transactions on Pattern Analysis and Machine Intelligence (PAMI), 2003, pp. 993-1008, vol. 25 Issue, IEEE.

Carter, William, "The advantage of single lens stereopsis," Stereoscopic Displays and Applications III, 1992, pp. 204-210, vol. 1669, SPIE.

FR0611491 Preliminary Search Report, mailed Mar. 26, 2010, 6 pages.

Guthart, Gary S. et al., "The IntuitiveT telesurgery system: overview and application," Proceedings of the 2000 IEEE International Conference on Robotics & Automation, 2000, pp. 618-621, vol. 1, IEEE.

Hart, Douglas P., "Second-Order Correlation," YAYOI Symposium on Particle Imaging Velocimetry (VSJ-SPIE98 Post-Conference Symposium), 1998, 14 pages.

Hart, Douglas P., "High speed PIV analysis using compressed image correlation," Journal of Fluids Engineering, 1998, pp. 463-470, vol. 120.

Hart, Douglas P., "Sparse array image correlation," 8th International Symposium on Applications of Laser Techniques to Fluid Mechanics, 1996, pp. 53-74, vol. 1 (Session 1).

Hart, Douglas P., "PIV Error Correction," 9th International Symposium on Applications of Laser Techniques to Fluid Mechanics, Jul. 13-16, 1998, Lisbon, Portugal, in Laser Techniques Applied to Fluid Mechanics: Selected Papers from the 9th International Symposium, 1998, pp. 19-36.

Hart, Douglas P., "PIV error correction," Experiments in Fluids, 2000, pp. 13-22, vol. 29—Issue 1, Springer-Verlag.

Hart, Douglas P., "Successive Approximation PIV Analysis to Achieve High Accuracy," Resolution, and Speed, The 13th U.S. National Congress of Applied Mechanics, 1998, 1 page.

Hart, Douglas P., "Super-Resolution PIV Processing by Recursive Correlation," Journal of Visualization,The Visualization Society of Japan, 2000, pp. 187-194, vol. 10.

Hidrovo, Carlos H. et al., "2-D thickness and Temperature Mapping of Fluids by Means of Two Dye Laser Induced Fluorescence Ratiometric Scheme," Proceedings of the 3rd Pacific Symposium on Flow Visualization and Image Processing, 2001, 30 pages.

Hidrovo, Carlos H. et al., "2-D thickness and Temperature Mapping of Fluids by Means of Two-Dye Laser Induced Fluorescence Ratiometric Scheme," Journal of Flow Visualization and Image Processing, 2002, pp. 171-191, vol. 9.

Hidrovo, Carlos H. et al., "Emission Reabsorption Laser Induced Fluorescence for Film Thickness Measurement," Measurement Science and Technology, 2001, pp. 467-477, vol. 12—Issue 4, Institute of Physics Publishing.

Horn, Berthold K.P. et al., "Determining Optical Flow, Artificial Intelligence," 1981, pp. 185-203, vol. 17.

Huang, Hayden et al., "Quantified flow Characteristics in a Model Cardiac Assist Device," Measurement and Instrumentation Forum, ASME Fluids Engineering Division Summer Meeting, Jun. 22-26, 1997, 6 pages.

Jojic, Nebojsa et al., "Tracking Self-Occluding Articulated Objects in Dense Disparity Maps," IEEE International Conference on Computer Vision, Corfu, 1999, pp. 123-130, vol. 1, IEEE.

Kavoussi, Louis R. et al., "Telerobotic Assisted Laparoscopic Surgery: Initial Laboratory and Clinical Experience," Urology, Jul. 1994, pp. 15-19, vol. 44—Issue 1.

(56) References Cited

OTHER PUBLICATIONS

Keith, Jack, ideo Demystified, A Handbook for the Engineer, 1993, pp. 338-356, HighText Publications, Inc., Solana Beach, CA, USA, ISBN: 1-878707-09-4.
Keramas, James G., "Robot Technology Fundamentals," 1999, pp. 193-219.
Kim, Yoon Sang, "Surgical Telementoring Initiation of a Regional Telemedicine Network: Projection of Surgical Expertise in the WWAMI Region," 3rd 2008 International Conference on Convergence and Hybrid Information Technology (ICCIT 08), Nov. 11-13, 2008, Busan, Korea, vol. 1, pp. 974-979, IEEE.
Lammerding, J. et al., "Monocular 3-D Magnetic Bead Microrheometry," 11th International Symposium on Application of Laser Techniques to Fluid Mechanics, 2002, 4 pages.
Lee, Benjamin R. et al., "A novel method of surgical instruction: international telementoring," World Journal of Urology, 1998, pp. 367-370, vol. 16—Issue 6, Springer Berlin / Heidelberg.
Lee C.H., et al., "Purification and Characterization of a Polysome-associated Endoribonuclease that Degrades c-myc mRNA in Vitro," The Journal of Biological Chemistry, 1998, vol. 273 (39), pp. 25261-25271.
Lin, Cheng-Hsien et al., "Ultrasound motion estimation using a hierarchical feature weighting algorithm," Computerized Medical Imaging and Graphics, 2007, vol. 31, pp. 178-190, Elsevier.
Link, Richard E. et al., "Telesurgery: Remote Monitoring and Assistance During Laparoscopy," Urol Clin North Am, 2001, pp. 177-188, vol. 28—Issue 1, Sanders.
Micali, S. et al., "Feasibility of telementoring between Baltimore (USA and Rome (Italy): the first five cases," J Endourol, 2000, pp. 493-496, vol. 14—Issue 6.
Moore, R.G. et al., "Telementoring of laparoscopic procedures: Initial clinical experience," Surgical Endoscopy, 1996, pp. 107-110, vol. 10—Issue 2, Springer-Verlag.
Official Action mailed Aug. 8, 2012 for JP Application No. 2006335952 filed Dec. 13, 2006.
PCT/US06/62381 International Search Report, mailed Jan. 2, 2008, 1 page.
PCT/US06/62381 Written Opinion of the International Search Authority, mailed Jan. 2, 2008, 6 pages.
PCT/US09/68427 International Search Report and Written Opinion of the International Searching Authority, mailed Nov. 23, 2010, 20 pages.
PCT/US09/68427 Partial International Search Report, mailed Jun. 18, 2010, 6 pages.
PCT/US10/35402 International Search Report and Written Opinion of the International Searching Authority, mailed Aug. 2, 2010, 16 pages.
Rafiq A., et al., "Digital Video Capture and Synchronous Consultation in Open Surgery," Annals of Surgery, 2004, vol. 239 (4), pp. 567-573.
Rafiq, Azhar et al., "SOCRATES: Telementoring for Telerobotics," and Todd Drasin et al., "Using Telerobots as Assistant Surgeons," Chapters 11 and 26: Primer of Robotic & Telerobotic Surgery, Garth H. Ballentyne et al., 2004, Ippincott Williams & Wilkins, pp. 78-85 and 188-195.
Rohaly, Janos et al., "High Resolution Ultrafast 3D Imaging," Proceedings of Photonics West 2000: Three Dimensional Image Capture and Application III, 2000, pp. 2-10, vol. 3958, SPIE.
Rohaly, Janos et al., "Monocular 3-D Active Micro-PTV," 4th International Symposium on Particle Image Velocimetry, 2001, pp. 1-4, paper No. 1147.
Rohaly, Janos et al., "Reverse Hierarchical PIV Processing," 4th International Symposium on Particle Image Velocimetry, 2001, 16 pages, paper No. 1009.
Saga, Sato et al., "A Method for Modeling Freehand Curves-the Fuzzy Spline Interpolation," Systems and Computers in Japan, Sep. 26, 1995, vol. 26, Issue 10, pp. 77-87, Scripta Technica, Inc.
Scharstein D., et al., A Taxonomy and Evaluation of Dense Two-Frame Stereo Correspondence Algorithm, Proceedings of the IEEE Workshop on Stereo and Multi-Baseline Vision, 2001, 10 pages.
Schulam Peter G. et al., "Telesurgical mentoring: Initial clinical Experience," Surgical Endoscopy, 1007, pp. 1001-1005, vol. 11, Springer-Verlag.
See, William A. et al., "Predictors of laparoscopic complications after formal training in laparoscopic surgery," Journal of the American Medical Association, 1993, pp. 2689-2692, vol. 270—Issue 22.
Stefano L.D., et al., "A Fast Area-Based Stereo Matching Algorithm," Image and Vision Computing, 2004, vol. 22, pp. 983-1005.
Stoianovici, Dan, "Robotic tools for minimally invasive urologic surgery," Chapter in Complications of Urologic Laparoscopic Surgery: Recongnition, Management and Prevention, published 2005 by Taylor Francis, paper dated Dec. 2002, 17 pages.
Thirouard, Benoist et al., "Investigation of Oil Transport Mechanisms in the Piston Ring Pack of a Single Cylinder Diesel Engine," Using Two-Dimensional Laser-Induced Fluorescence, SAE Transactions: Journal of Fuels and Lubricants, 1998, pp. 2007-2015, vol. 107—Issue 4.
Trucco, E. et al., "Real-Time Disparity Maps for Immersive 3-D Teleconferencing by Hybrid Recursive Matching and Census Transform," Dept. of Computing and Electrical Engineering, 2001, 9 pages.
Tzovaras, Dimitrios et al., "Disparity field and depth map coding for multiview 3D image generation," Signal Processing: Image Communication, 1998, pp. 205-230, vol. 11, Elsevier.
Wu, Chun-Hong et al., "Depth Mapping of Integral Images through Viewpoint Image Extraction with a Hybrid Disparity Analysis Algorithm," Journal of Display Technology, Mar. 2008, vol. 4, Issue No. 1, pp. 101-108, IEEE.
Chinese Application Serial No. 201080027164.3, Office Action mailed Dec. 20, 2013, 9 pgs.
Japanese Application Serial No. 2012-516111, Office Action mailed Dec. 12, 2013, 2 pgs.
Chinese Application Serial No. 201080027165.8, Response filed Jul. 29, 2013 to Office Action mailed Jan. 20, 2014, (w/ English Translation of Claims), 11 pages.
Japanese Application Serial No. 2012-516098, Argument and Amendment filed Jun. 10, 2014 in response to Office Action mailed Dec. 12, 2013, (w/ English Translation of Amended Claims), 20 pages.
Office Action mailed Nov. 4, 2014 for Chinese Application 201080027165.8 filed May 19, 2010, 30 pages.
Office Action mailed Dec. 22, 2014 for Japanese Application No. 20120516098 filed May 19, 2010.
Office Action mailed Dec. 22, 2014 for Japanese Application No. 20120516111 filed Jun. 3, 2010.
"Chinese Application Serial No. 201080027164.3, Office Action mailed Nov. 3, 2014", 15 pgs.
"Japanese Application Serial No. 2012-516111, Final Office Action mailed Dec. 22, 2014", 8 pgs.

* cited by examiner

| Polyline3D |
|---|
| +AddPoint(pt: Point3D): void<br>+AddPoint(x: double, y: double, z: double): void<br>+RemoveLastPoint(): void<br>+Clear(): void<br>+GetNumPoints(): unsigned<br>+SetPoint(index: unsigned, pt: Point3D): bool<br>+SetPoint(index: unsigned, x:double, y: double, z: double): bool<br>+GetPoint(index: unsigned, pt: Point3D): bool<br>+ComputeCentroid(centroid: Point3D): void<br>+Compute Length(bClosed: bool): double<br>+ComputeArea(): double<br>+Compute Bounds(lo: Point3D, hi: Point3D): void<br>+ComputePointNormal(index: unsigned, center: Point3D, normal: Point3D): bool<br>+Compute LoopNormal(normal: Point3D): bool |

FIG. 10A

| PolylineGLMapper |
|---|
| +<u>New(): PolylineGLMapper</u><br>+Render(ren: vtkRenderer, a: vtkActor): void<br>+GetBounds(): double<br>+SetPolyline(polyline: Polyline3D): void<br>+GetPolyline(): Polyline3D<br>+GetPolyIne(): Polyline3D<br>+SetDrawMode(nMask: unsigned): void<br>+GetDrawMode(): unsigned<br>+SetClosedLoop(bClosed: bool): void<br>+IsClosedLoop(): bool<br>+SetUseStipple(bStipple: bool): void<br>+GetUseStipple(): bool<br>+SetUseWireframe(bWireframe: bool): void<br>+GetUseWireframe(): bool<br><<create>>-PolylineGLMapper()<br><<destroy>>-PolylineGLMapper()<br>#DtawLines(): void<br>#DrawPoints(): void<br># DrawSurface(): void<br><<create>>-PolylineGLMapper(: PolylineGLMaper) |

FIG. 10B

VIRTUAL MEASUREMENT TOOL FOR MINIMALLY INVASIVE SURGERY

CROSS-REFERENCES TO RELATED APPLICATIONS

The present application is related to U.S. patent application Ser. No. 12/428,691 (filed Apr. 23, 2009), Ser. No. 12/465,029 (filed May 13, 2009), and Ser. No. 12/485,503 (filed concurrently) entitled "Virtual Measurement Tool For Minimally Invasive Surgery", the full disclosures of which are incorporated herein by reference.

STATEMENT AS TO RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND

The present invention is generally related to improved robotic and/or measurement devices, systems, and methods. An exemplary embodiment provides a robotic surgical system which makes use of a combination of telemanipulation of a robotic tool together with stereoscopic image processing to input and designate discrete three-dimensional (3-D) point locations along the tissue (or other structure), continuous 3-D contours, and other 3-D structural information so as to obtain length measurements, area measurements, volume measurements, or the like.

Minimally-invasive surgical techniques are aimed at reducing the amount of extraneous tissue that is damaged during diagnostic or surgical procedures, thereby reducing patient recovery time, discomfort, and collateral tissue damage. As a consequence, the average length of a hospital stay for standard surgery may be shortened significantly using minimally-invasive surgical techniques. Also, patient recovery times, patient discomfort, surgical side effects, and time away from work may also be reduced with minimally-invasive surgery.

Endoscopy is a well known form of minimally-invasive surgery, and a common form of endoscopy is laparoscopy, which is minimally-invasive inspection and surgery inside the abdominal cavity. In standard laparoscopic surgery, a patient's abdomen is insufflated with gas and cannula sleeves are passed through small (approximately ½ inch or less) incisions to provide entry ports for laparoscopic instruments.

Laparoscopic surgical instruments generally include a laparoscope or an endoscope (for viewing the surgical field), and working tools. The working tools are similar to those used in conventional open surgery, except that the working end or end effector of each tool is separated from its handle by an elongate shaft. The end effector or working part of the surgical instrument can manipulate or treat tissue, and may (for example) include clamps, graspers, scissors, staplers, image capture lenses, or needle holders.

To perform surgical procedures, the surgeon passes the working tools or instruments through cannula sleeves to an internal surgical site and manipulates the tools or instruments from outside the abdomen. The surgeon views the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

Minimally-invasive telesurgical robotic systems are being developed to increase a surgeon's dexterity when working within an internal surgical site, and optionally to allow a surgeon to operate on a patient from a remote location. In a telesurgery system, the surgeon is often provided with an image of the surgical site at a control console. While viewing a 3-D image of the surgical site on a suitable viewer or display, the surgeon performs the surgical procedures on the patient by manipulating master input or control devices of the control console. Each of the master input devices controls the motion of a servomechanically operated surgical instrument. During the surgical procedure, the telesurgical system can provide mechanical actuation and control of a variety of surgical instruments or tools having end effectors that perform various functions for the surgeon, e.g., holding or driving a needle, grasping a blood vessel, dissecting tissue, or the like, in response to manipulation of the master input devices.

While the new telesurgical robotic systems have tremendous promise for extending the capabilities of surgeons to perform therapies with less trauma to the patient, as with many successes, still further improvements would be desirable. For example, known robotic systems often rely on joint position information from sensors associated with each of the joints of the robotic linkage to calculate end effector movement demands, locations, and the like. While such joint-based information provides sufficiently accurate relative movements of the end effector for most telesurgical purposes, the absolute location of the surgical tool determined using this joint-based data may not be precise enough for all purposes. In particular, there are times when it would be advantageous to acquire tissue measurement information using the robotic surgical system, and some improvement over the accuracy provided by the joint-based data may be beneficial for such measurements.

In light of the above, it would be desirable to provide improved robotic and/or measurement systems for surgery and other applications. It would be particularly advantageous if these improvements allowed the physician to both interact with and measure tissues, ideally with the measurements comprising three dimensional measurements with accuracies beyond those easily provided using joint-based data alone.

SUMMARY

Aspects of the present invention generally provide improved robotic and/or measurement devices, systems, and methods. Embodiments of the invention may find use in telesurgical therapies through minimally invasive apertures such as an endoscopic cannula sleeve, a natural orifice, or the like. Such embodiments may employ telesurgical input devices operatively coupled to surgical tools so as to allow a system user to manipulate and otherwise interact with the tissues being measured. Rather than merely relying on joint-based data, the system may make use of three-dimensional (3-D) position information garnered from stereoscopic images, with the images also being presented to the system user. In addition to 3-D positional offsets between two or more discrete points on the tissue, the system may also allow the user to identify an effectively continuous curving line of positions along a tissue of interest. The system can then determine a length measurement of a 3-D line segment, a poly-line measurement of cumulative lengths along a straight or curving tissue, a measurement of the area within a tissue structure, a tissue volume measurement, an aspect ratio, or the like. The discrete points may be identified by a single surgical tool or by a separation between two or more surgical tools, with the user optionally measuring the length of a tissue structure (even a structure longer than a field of view of the stereoscopic image capture device or which is partially obscured) by walking a pair of tools "hand-over-hand" along the tissue structure, optionally while straightening or stretching the tissue structure. By allowing the system user to interact with the tissues while identifying the tissue locations to be measured, and by employing imaging data (optionally in combination with joint-based data) to determine the measurements, the measurement accuracy and ease of tissue measurements can be significantly enhanced, particularly when working with tissues that are at least partially obscured.

In a first aspect, the invention provides a method for measuring a structure. The method comprises grasping a first structure location with a first robotic tool jaw. A second structure location is grasped with a second robotic tool jaw. The jaws of the first tool are released, and the first tool is moved from the first location so as to grasp a third structure location. Three-dimensional offsets between the locations are summed so as to measure a hand-over-hand length along the structure.

The structure being measured will often include a tissue structure within a minimally invasive surgical site, with the structure optionally being an elongate and/or flexible tissue structure such as a portion of the gastrointestinal tract or the like. A plurality of additional tissue structure locations can be indicated by alternatingly grasping the structure with the first and second robotic tool jaws. The tissue structure can then be measured as a sequential series of offsets, with each offset defined by a pair of the locations-one being established using the first jaw, the other being established by the second jaw. A measurement location along each jaw can be superimposed on a display of the site so as to indicate whether the offset is being measured at the tips of the jaws, the middle of the jaws, the pivot points of the jaws, or the like. Similarly, a stretch line between the first and second jaws, an incremental offset measurement between the first and second jaws, and/or a cumulative measurement (including the previously summed offsets) can be superimposed.

The tissue locations will often be designating by actuation of the jaws, although alternative input mechanisms might be used. Preferably, releasing of the jaws of the first tool while the second tool continues to grasp the tissue designates the tissue location (and measures the offset) being grasped by the jaws of the second tool, and it also initiates an incremental offset measurement between the first location and the second location. This designation of the second location by releasing the first tool allows the second tool to grasp and release a plurality of candidate tissue locations without altering the summed offsets. This or other techniques can also be used to facilitate manipulating the tissue structure with the jaws so as to straighten or stretch a measured length of the tissue structure before an associated offset between the first and second jaws is determined. In other words, for any given measurement, one tool may remain grasped and the other tool can be allowed to grasp and release multiple times until a desired tissue location is achieved. At that point, the other tool may be released to commit the measurement. The location designating responsibilities between the tools can then be swapped.

In many embodiments the user will view the tissue structure within a field of view of an image capture device. Some of the tissue structure may not be visible in the field of view while determining an offset between the first location and the second location. The tissue structure may be manipulated with the jaws so as to image the previously obscured portion into view. Alternatively, the field of view may be moved so as to image a previously unseen location along the structure and allow the measurement to include an offset between associated grasped locations. Preferably, capturing left and right stereoscopic images of the tissue structure are obtained with an image capture device that generates image data. The offsets can then be measured by determining three dimensional offsets between the locations using the image data.

In another aspect, the invention provides a method for measuring tissue. The method comprises indicating a first tissue location with a first robotic tool. A plurality of additional tissue locations are also robotically indicated. A measurement defined by the tissue locations is determined.

In many embodiments the measurement comprises a cumulative length between pairs of the tissue locations, and/or an area measurement. Still further options include the measurement of an aspect ratio defined by the locations, or the like. In some embodiments a center location within the area can be identified and areas of triangles defined between the center and the tissue locations so as to calculate the area. Line segments between the locations may be superimposed on an image of the tissue, with the segments often presenting a border of the area. The system user will often robotically direct movement of the first tool with reference to the image.

The image may be acquired with an image capture device that generates image data, and the tissue locations may be determined in response to the image data. The tissue locations will typically comprise discretely designated locations bordering the area with each location being designated per an associated input from a system user. In some embodiments the locations are designated in response to a temporal or spatial separation between the first robotic tool and a prior location, with the locations optionally being spaced closely so as to appear to the user as a continuous curving line tracking a movement of the tool. A graphical indicator may be superimposed within an image of the tissue at each of the locations. The graphical indicators may persist after the first tool has been displaced from locations designated by the first tool. Lines may be superimposed between sequential locations within the image, a graphical indicator may be superimposed on a tool measurement location of the first robotic tool (such as at the tool tip, at a midpoint along a pair of jaws, or the like) within the image, and/or a stretch line may be superimposed between an immediately prior location and the tool within the image. An incremental offset between the immediately prior location and the tool may be superimposed within the image, a cumulative summation of the offsets, an area, a volume, and/or the like may be superimposed on the image, with these measurements often being offset from the locations and/or any lines connecting them.

In some embodiments, the locations may indicated using two or more robotic tools. Measurements using more than two tools may optionally be per the input of multiple system users. For example, a second robotic tool may indicate at least a second tissue location and a third robotic tool may indicate at least a third tissue location. The first robotic tool may be operatively associated with a first master/slave three dimensional input device operated by a first surgeon or other system user and the second robotic tool can be operatively associated with a second master/slave three dimensional input device operated by a second surgeon or other system user.

In another aspect, the invention provides a system for measuring structures. The system comprises a first robotic tool jaw for grasping a first structure location. A second tool jaw grasps a second structure location. The processor couples the robotic tools to an output such that an input command from the operator induces the processor to sum 3-D offsets between the locations so as to measure a hand-over-hand length along the structure.

In another aspect, the invention provides a system for measuring tissue. The system comprises a first robotic tool for engaging a first tissue location. A processor is coupled to the first tool so that the processor determines a measurement defined by the first tissue location and a plurality of additional robotically engaged locations.

BRIEF DESCRIPTION OF THE DRAWINGS

FIGS. 10A and 10B are class diagrams for area or container computation and display.

DETAILED DESCRIPTION

Aspects of the present invention generally provides improved robotic and/or measurement devices, systems, and methods, particularly for telesurgery and other medical robotic applications. Embodiments of the present invention may find their most immediate use for measurement of tissues and other structures located at an internal surgical site accessed through one or more minimally invasive apertures (such as a cannula or natural orifice). Work in connection with the present invention has indicated that measurement at such a site may be enhanced by engaging and/or manipulating the tissues to be measured using a robotic surgical tool. While robotic manipulations can be performed with very good precision using joint-based data from the robotic linkage to calculate movement commands, measurement accuracy within an internal surgical site may be enhanced by employing image processing of stereoscopic imaging data to help determine the locations of tissue and/or robotic surgical tools within the internal surgical site. By superimposing appropriate indicia on the stereoscopic images presented to a system user, the user can accurately designate tissue or other structure locations and measure contours (including smoothly curving contours and/or series of line segments) in three-dimensional (3-D) space so as to determine lengths, areas, volumes, and the like.

Figure 1:
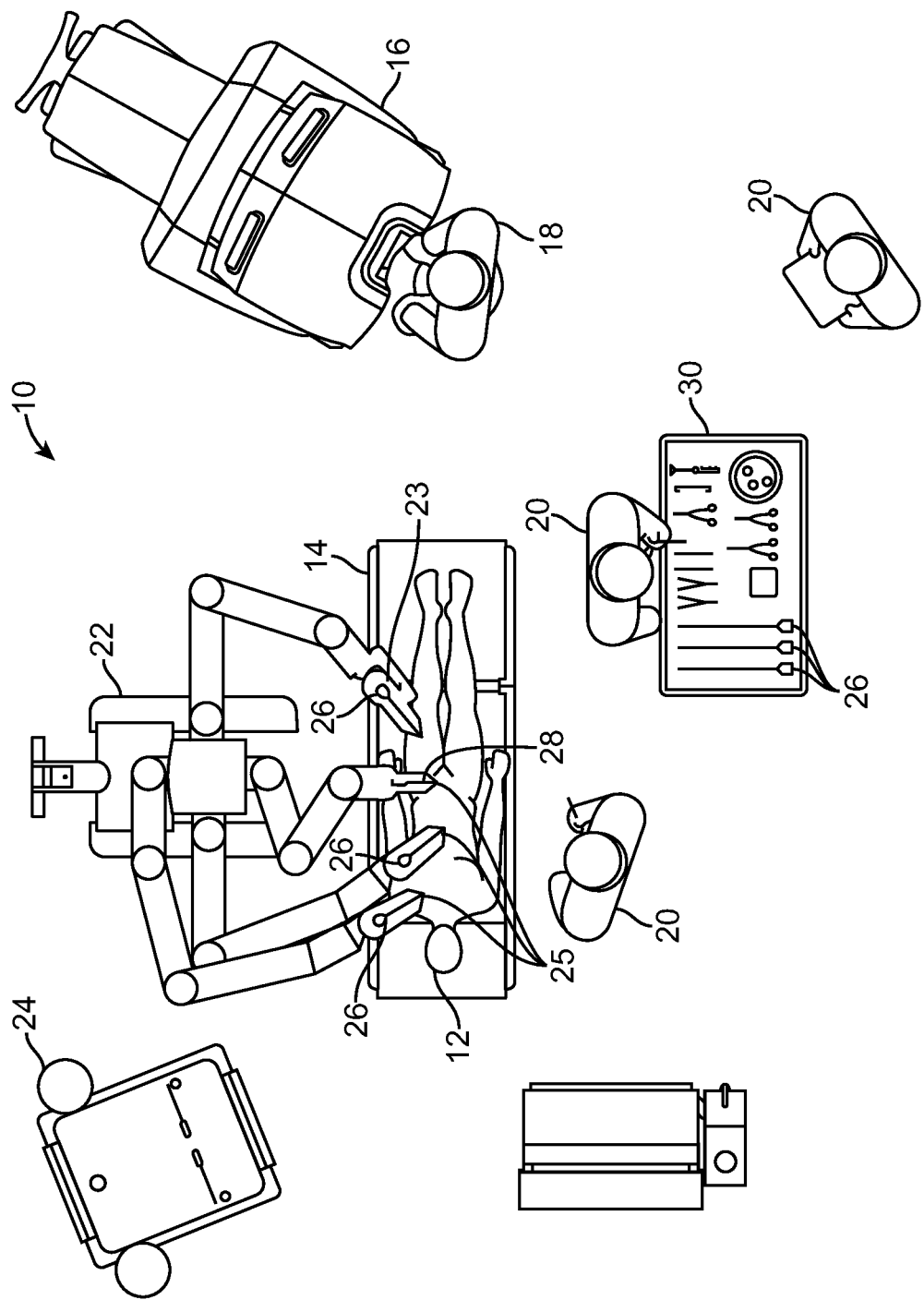
FIG. 1 is a plan view of a minimally-invasive robotic surgery system being used to perform a surgery, in accordance with embodiments of the invention.

FIG. 1 is a plan view illustration of a Minimally-Invasive Robotic Surgical (MIRS) system 10, typically used for performing a minimally-invasive diagnostic or surgical procedure on a Patient 12 who is lying on an Operating table 14. The system can include a surgeon's console 16 for use by a Surgeon 18 during the procedure. One or more Assistants 20 may also participate in the procedure. The MIRS system 10 can further include a patient side cart 22 (surgical robot), and a vision cart 24. The patient side cart 22 includes manipulators 23, which can manipulate at least one removably coupled instrument or tool assembly 26 (hereinafter simply referred to as a "tool") through a minimally invasive incision in the body of the Patient 12 while the Surgeon 18 views the surgical site through the console 16. An image of the surgical site can be obtained by an endoscope 28, such as a stereoscopic endoscope, which can be manipulated by another manipulator 23 of the patient side cart 22 so as to position and orient the endoscope 28. The vision cart 24 can be used to process the images of the surgical site from the endoscope 28 for subsequent display to the Surgeon 18 through the surgeon's console 16. The number of surgical tools 26 used at one time will generally depend on the diagnostic or surgical procedure and the space constraints within the operating room among other factors. Optionally, more than one Surgeon's console may be provided, particularly when three or more tools will be used, thereby allowing two surgeon to collaborate, transfer control of instruments, and the like as more fully explained in U.S. Pat. No. 6,659,939 (filed Nov. 3, 1999), the disclosure of which is incorporated herein by reference. If it is necessary to change one or more of the tools 26 being used during a procedure, an Assistant 20 may remove the tool 26 no longer being used at the time from the patient side cart 22 and replace it with another tool 26 from a tray 30 in the operating room.

Figure 2:
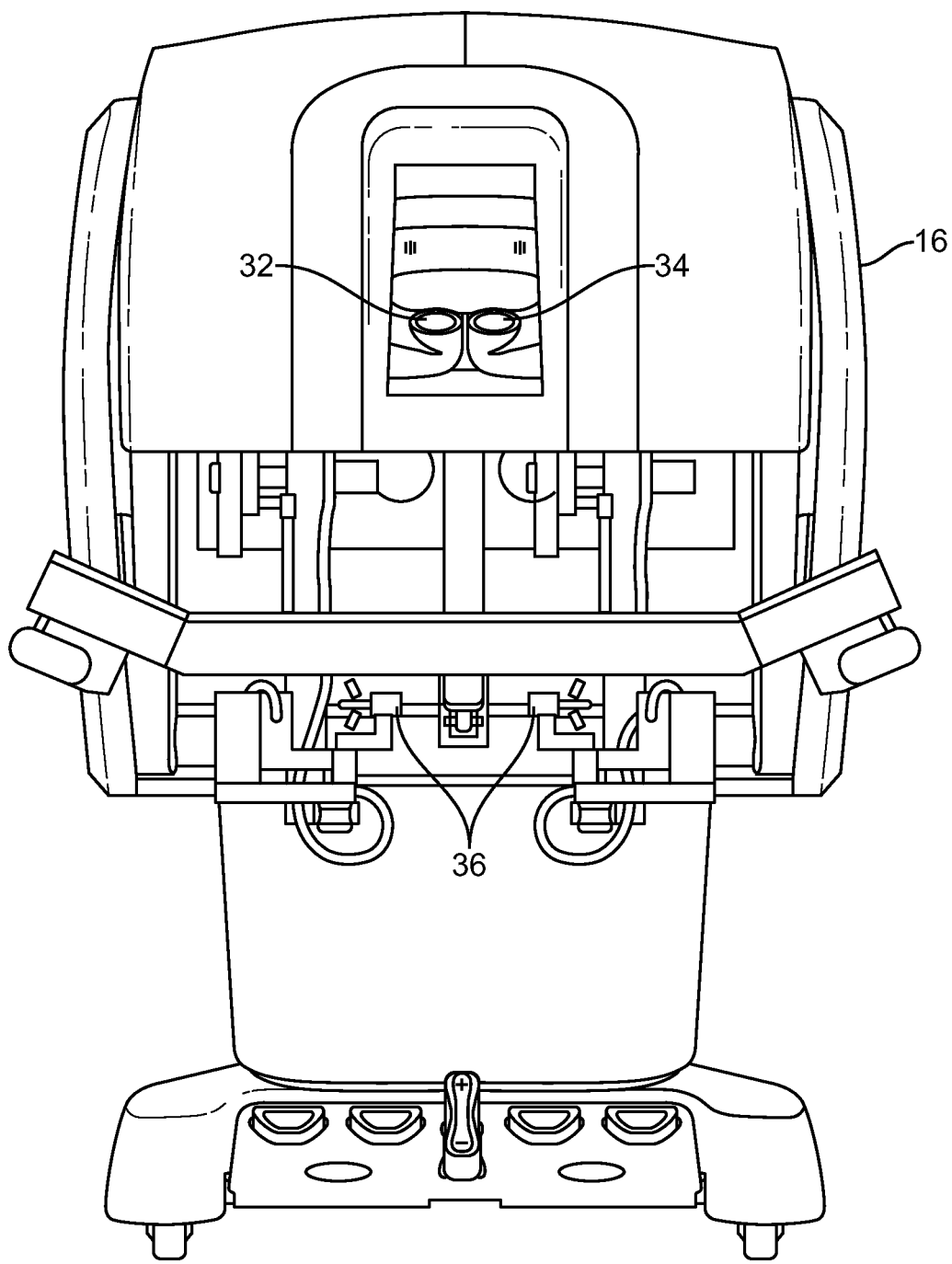
FIG. 2 is a front view of a surgeon's control console for a robotic surgery system.

FIG. 2 is a front side view of the surgeon's console 16. The surgeon's console 16 includes a left eye display 32 and a right eye display 34 for presenting the Surgeon 18 with a coordinated stereo view of the surgical site that enables depth perception. The console 16 further includes one or more control devices 36 (masters), which in turn cause the patient side cart 22 (shown in FIG. 1) to manipulate one or more tools (slaves). Preferably, control devices 36 will provide the same degrees of freedom as their associated tools 26 (shown in FIG. 1) so as to provide the Surgeon with telepresence—the perception that the control devices 36 are integral with the tools 26 so that the Surgeon has a strong sense of directly controlling the tools 26. To this end, position, force, and tactile feedback sensors (not shown) are optionally employed to transmit position, force, and tactile sensations from the tools 26 back to the Surgeon's hands through the control devices 36.

The surgeon's console 16 is usually located in the same room as the patient so that the Surgeon may directly monitor the procedure, be physically present if necessary, and speak to an Assistant directly rather than over the telephone or other communication medium. However, it will be understood that the Surgeon can be located in a different room, a different building, or other remote location from the Patient, thus allowing for remote surgical procedures.

Figure 3:
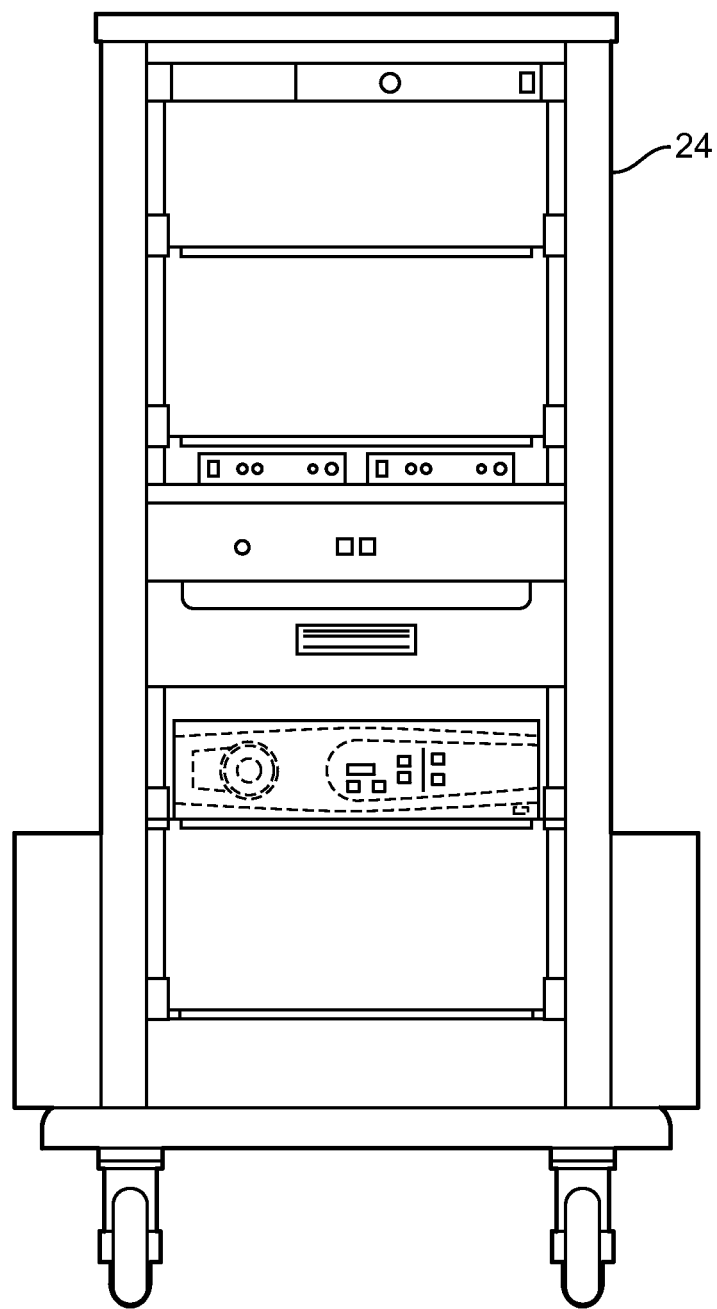
FIG. 3 is a front view of a robotic-surgery system vision cart.

FIG. 3 is a front view of a vision cart 24. Vision cart 24 can be coupled with the endoscope 28 and can include a processor to process captured images for subsequent display, such as to a Surgeon on the surgeon's console, or on any other suitable display located locally and/or remotely. For example, where a stereoscopic endoscope is used, the vision cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations. Exemplary details of some of the possible image processing that can used are described in numerous patents and patent applications assigned to Intuitive Surgical, Inc. including, for example in U.S. Pat. No. 7,277,120 (filed Mar. 7, 2004), the full disclosure of which is incorporated herein by reference.

Figure 4:
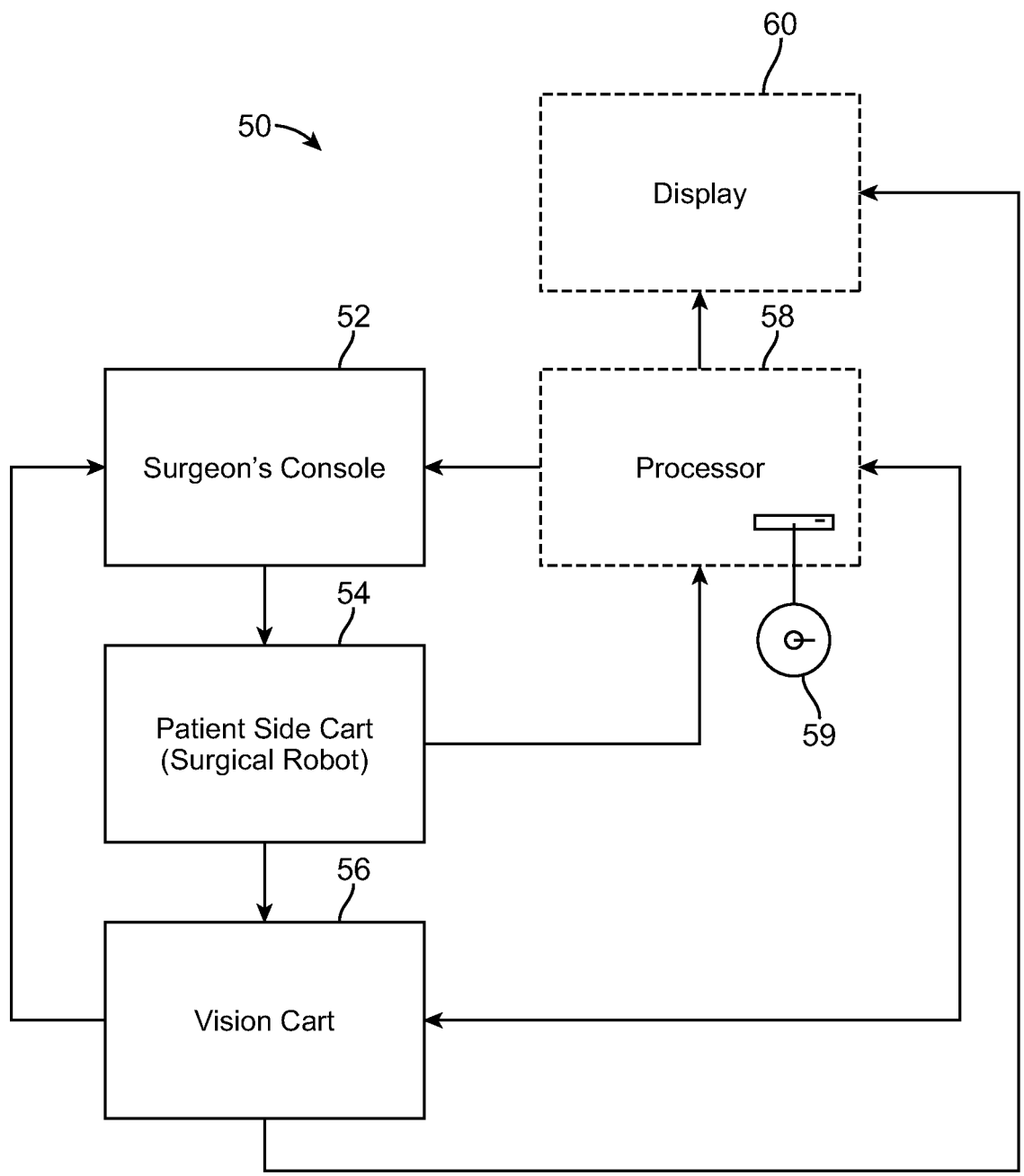
FIG. 4 diagrammatically illustrates data processing structures of the robotic surgery system of FIG. 1.

FIG. 4 diagrammatically illustrates a robotic surgery system 50 (such as MIRS system 10 of FIG. 1), showing communication paths between components. As discussed above, surgeon's console 52 (such as surgeon's console 16 in FIG. 1) can be used by a Surgeon to control a patient side cart (surgical robot) 54 (such as patient side cart 22 in FIG. 1) during a minimally-invasive procedure. The patient side cart 54 can use an imaging device, such as a stereoscopic endoscope, to capture images of the procedure site and output the captured images to a vision cart 56 (such as vision cart 24 in FIG. 1). Vision cart 56 can process the captured images in a variety of ways prior to any subsequent display. Alternatively, the patient side cart 54 can output the captured images for processing outside the vision cart 56. For example, the patient side cart 54 can output the captured images to a processor 58, which can be used to process the captured images. The images can also be processed by a combination the vision cart 56 and the processor 58, which can be coupled together so as to process the captured images jointly, sequentially, and/or combinations thereof. One or more separate displays 60 can also be coupled with the processor 58 and/or the vision cart 56 for local and/or remote display of images, such as images of the procedure site, or any other related images.

Each of the processors described herein will typically include tangible media (e.g., one or more locations and/or storage types) 59 embodying computer-readable instructions or software for implementing some or all of the method steps described herein. Tangible media 59 may comprise an optical recording media such as a compact disk or digital video disk, a magnetic recording media such as a hard disk drive, a floppy disk, a backup tape, or the like, a memory such as a read-only memory, a random access memory, a non-volatile memory, a memory stick, or the like. The software or code stored in tangible media 59 may be transmitted to the processor via the tangible recording media, an internet or other network system, a wireless signal transmission, or the like. While schematically shown in FIG. 4 as the tangible media associated with processor 58, the software may reside in a number of different processors, including processors of the surgeon's console 52, patient side cart 54, vision cart 56, and/or processor 58. Hence, the software may run on one or more processor circuits or processor boards that are physically mounted to one or more of the components of the robotic surgery system 50 in any of a wide variety of centralized or distributed data processing system architectures. Similarly, the software may be written as a single monolithic code, but it will often be broken down into a series of subroutines, with differing portions of the code optionally running on differing processor boards. The functionality attributed to modules described herein will often be implemented as software (including software code embodied on tangible media 59), hardware (including a processor circuit of processor 58 or one of the other processor boards of robotic surgical system 50), and/or a combination of software and hardware suitable for the ascribed data processing tasks.

Figure 5C:
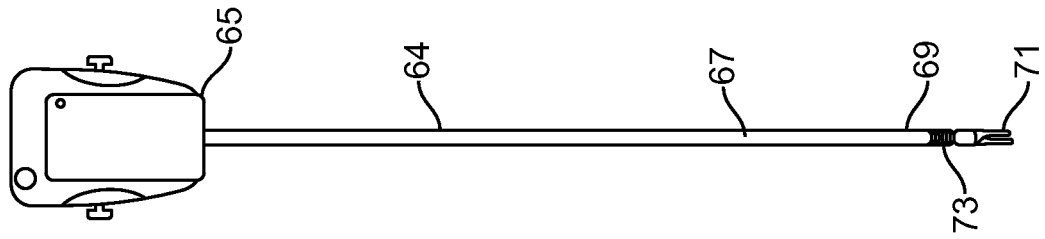
FIGS. 5B and 5C are respective front views of an 8 mm shaft robotic surgery tool and a 5 mm shaft robotic surgery tool.
Figure 5B:
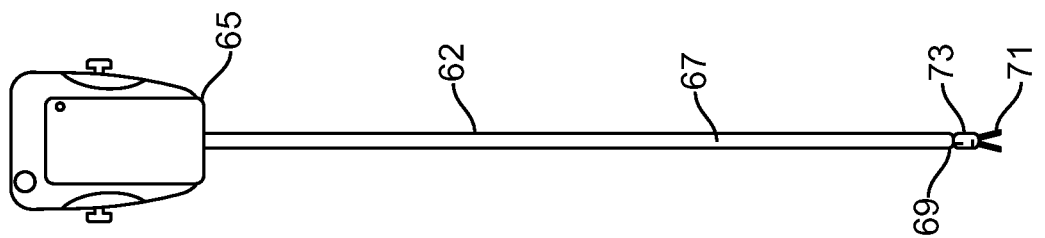
Figure 5A:
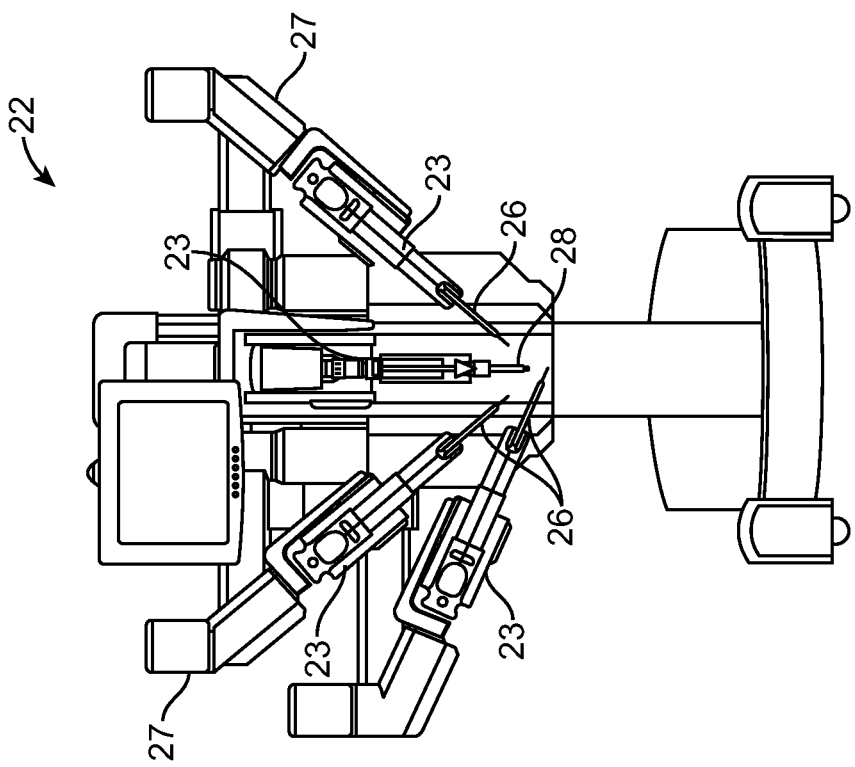
FIG. 5A is a front view of a patient side cart (surgical robot) of a robotic surgery system.

FIGS. 5A, 5B, and 5C show a patient side cart 22, an 8 mm shaft surgical tool 62, and a 5 mm shaft surgical tool 64, respectively. Surgical tools 62 and 64 are examples of surgical tools 26. The patient side cart 22 shown provides for the manipulation of three surgical tools 26 and an imaging device 28, such as a stereoscopic endoscope used for the capture of images of the site of the surgical procedure. Manipulation is provided by robotic mechanisms having a number of robotic joints. The imaging device 28 and the surgical tools 26 (e.g., the end effectors 66) can be positioned and manipulated through incisions in the patient so that a kinematic pivotal center 25 (see FIG. 1) is maintained at the incision so as to minimize the size of the required incision. Images of the surgical site can include images of distal ends of the surgical tools 26 when they are positioned within the field of view of the imaging device 28.

As can be understood with reference to FIGS. 1 and 5A, each tool 26 is typically supported by a manipulator 23. The manipulator moves during surgery under the direction of a processor of surgeon's console 16 so as to move an end effector of the tool within the internal surgical site per an input movement command. Manipulators 23 are generally supported by a passive support linkage 27 so as to allow the manipulators and tools to be positioned manually in preparation for surgery. The support linkages 27, sometimes referred to as set-up arms (which include one or more unpowered, lockable set-up joints), also allow the position and orientation of tools to be changed during a procedure, with an assistant 20 typically withdrawing the tool, releasing the set-up joints from a fixed configuration to a manually movable configuration, moving the manipulator 23 to a new and desired location, and again fixing the set-up joints. Joint-based data is provided from both the manipulator 23 and the support linkage 27 to the processor of the surgeon cart 16 for calculation of movement commands in response to the input from the surgeon 18.

Referring now to FIGS. 5B and 5C, tools 62, 64 typically include a proximal end 65 supportable by a manipulator 23, and an elongate shaft 67 that extends from the proximal end to a distal end 69. An end effector 71 is coupled to distal end 69 of shaft 67 by a linkage 73, with the end effector and linkage generally being driven by motors of linkage 23. In alternative embodiments, at least some of the degrees of freedom of the set-up joints may be powered, and/or some of the degrees of freedom of the manipulator may be passive. The pivotal center may be defined by a parallel linkage structure of manipulator 23 (encompassed within the term remote center linkage), or a passive joint of the manipulator may allow for natural or environmentally imposed pivoting of the tool about the aperture into the patient. Still further alternatives are possible, including redundant-joint driven linkages, which allow a calculated remote center of pivotal movement to be provided.

Figure 6:
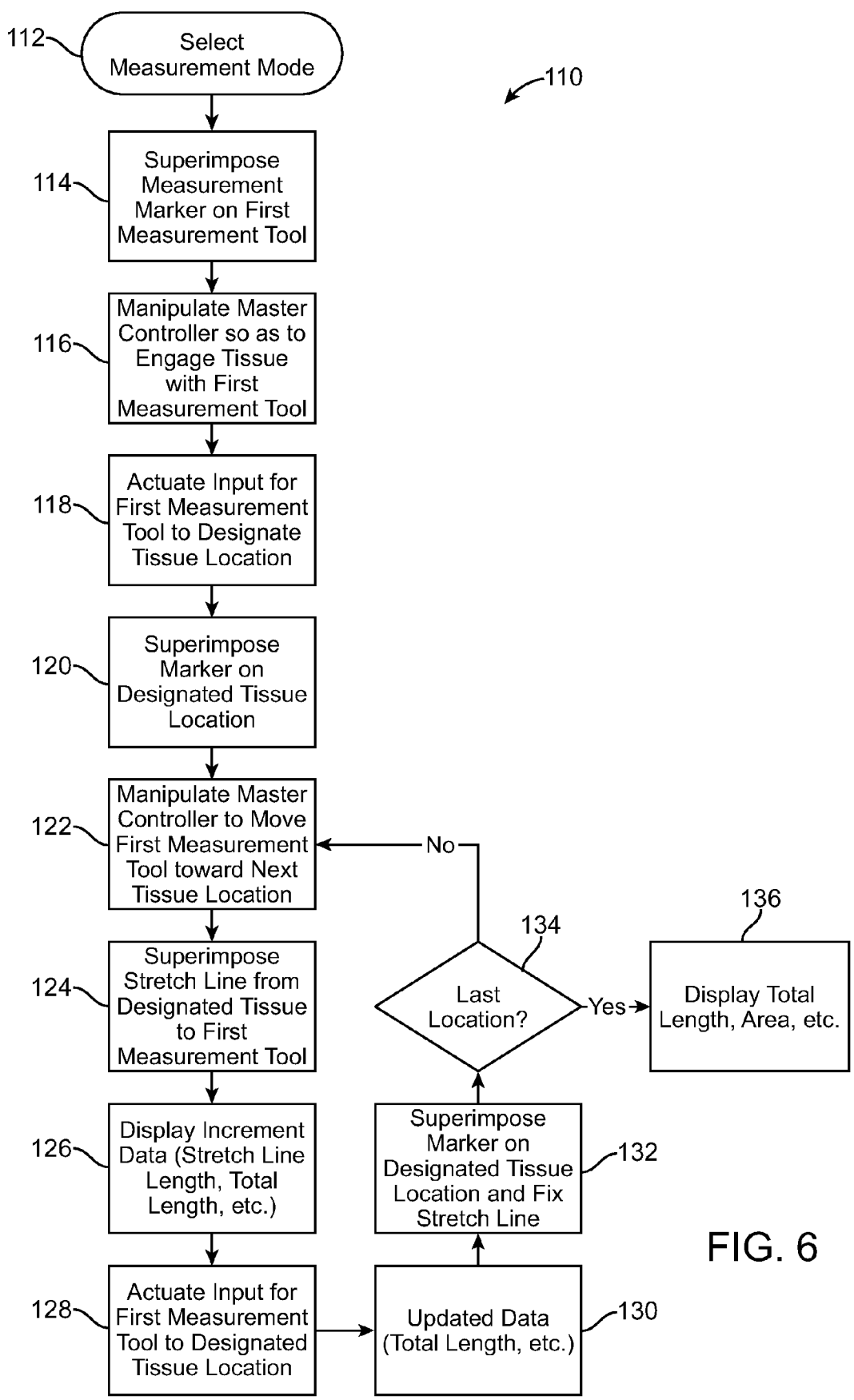
FIG. 6 schematically illustrates steps included in a method for measuring tissue using the system of FIG. 1.

Referring now to FIG. 6, a method 110 for measurement using robotic system 50 can be understood. The measurement may be initiated by selecting the measurement mode 112 using a foot pedal, pull down menus, an auxiliary input device (such as a keyboard, mouse, or the like), verbal command to the robotic system or an assistant, or any of a wide variety of alternative approaches. A measurement marker or other indicia may be superimposed 114 on a measurement tool. Where only one tool will be used to perform a measurement, it is helpful for the system user to have a visual indication regarding which of the tools is the measurement tool. Similarly, it may be helpful to have an indication that both tools will be used for the measurement, and/or for the measurement location on the tool to be identified (so that the user does not measure from the pivot point of the jaws, for example, when the system will calculate the offset from a distal tip of engagement surfaces between the jaws). The user may select or change which tool is used as the measurement tool, so as to designate a tool controlled by the dominant hand (the right hand of a right-handed surgeon, for example) as explained in more detail below. While measurements will often be described with reference to input from a single user controlling one or two instruments, coordinated motion of more than 2 instruments will optionally be employed, particularly when designating three or more locations, when simultaneously configuring tissue at three or more locations for measurement, and/or the like. Embodiments of the systems and methods described herein that employ three or more tools may benefit from input devices that accommodate simultaneous three dimensional input from multiple system users. For example, a dual surgeon's console arrangement can be used to facilitate the collaboration of two surgeons while they control three or more instruments at once.

To actually take a measurement, a system user will typically manipulate a master controller 116 (e.g., control device 36 in FIG. 2) so as to indicate a tissue location with a measurement tool. The system user may optionally engage the tissue at the location, such as lightly touching the tool to the tissue, palpating the tissue, or even grasping and reconfiguring the tissue. Alternatively, the user may bring the tool to a location close enough to the tissue to be an accurate point designation without actually touching the tissue. The use of the tool can allow the user to be confident that the point designation is valid even without touching the tissue, and verifying the location marker positioning on the marker can further enhance marker accuracy, repeatability, and confidence. Nonetheless, making contact with tissue can provide a useful visual cue to confirm that the instrument tip is at the intended depth.

Once the measurement marker of the tool is at the desired location, the user may then actuate an input (such as by opening and/or closing a handle of a master controller, optionally the one master controller associated with the measurement tool or a different master controller, by depressing a foot pedal, or the like) so as to designate a tissue location 118 to the system. The system can then superimpose a marker of the designated tissue location 120. Erroneously designated locations may optionally be removed by an alternative input, such as by actuating the handle of the master controller associated with the non-dominant hand. Note that the superimposing of markers on the image of the stereoscopic display and determining the tool location data may be implemented using processor 58 as shown in FIG. 4, by a processor of the vision cart 56, by a processor of the surgical robot 54, or by an alternative processor structure. The tissue location information may include and/or make use of information provided from robotic data output from patient side cart 54, with the robotic data often comprising joint-based data from the surgeon's console 52 and from the patient side cart 54. Three-dimensional position data corresponding to the designated tissue location will often be based at least in part on stereoscopic or other image capture devices. In some embodiments, at least some of the information regarding locations of the tools within the surgical site may be provided by processing the data displayed as images of the tools and surgical site displayed to the system user (as more fully described in co-pending U.S. patent application Ser. No. 12/428,691 (filed Apr. 23, 2009), previously incorporated herein by reference, and/or from any of a wide variety of alternative image-based tool tracking systems.

As noted above, the interaction between the tissue and tool during indication of the tissue location with the robotic tool may range from being near (but not touching) the tissue to actively grasping and reconfiguring the tissue. For example, the tool may reposition the tissue structure to be measured, optionally grasping the tissue, straightening the tissue structure, bringing the structure out from behind an intervening tissue or other object and into the field of view of the camera, or the like. In some embodiments the tool will palpate the tissue, optionally so as to indicate a location below a soft tissue surface, enhance accuracy and repeatability of designation of the measurement location(s), and/or the like. In embodiments where the tool is separated slightly from the tissue surface, a variety of image matching techniques can be combined with data from a calibrated stereoscopic camera (e.g., one calibrated using the structures and techniques described in U.S. patent application Ser. No. 12/415,377 (filed Mar. 21, 2009), the full disclosure of which is incorporated herein by reference, so as to determine a 3-D location of the tissue surface and/or structure. In general terms, the location of a surface, feature, or structure in left and right images, together with the calibration information, can be used to determine the horizontal position (X-Y) of the structure relative to the camera and the distance (Z) between the camera and that surface, feature, or structure. As described in more detail in U.S. Patent Application No. 61/204,082 (filed Dec. 31, 2008), the full disclosure of which is incorporated herein by reference, selective robust image matching between the left and right stereoscopic images can efficiently and robustly identify corresponding left and right images of one or more selected points on a tissue surfaces in the surgical field. Related techniques can be used to determine the location of the tool, optionally with the assistance of appropriate tool markers, as more fully described in U.S. Patent Application No. 61/203,975 (filed Dec. 31, 2008), also incorporated herein by reference.

In the exemplary sparse image matching technique, points of interest from a first image are identified for matching to the second image. Such points of interest might be identified by locating a tool tip or the like over the desired location or point on the tissue surface, optionally such that the tip is disposed on the point as seen in the dominant eye of the system user though the tool remains slightly separated from the tissue surface (more specifically between the tissue surface and the camera). The selectively identified points of interested can be matched to the second image (optionally as shown to the non-dominant eye) with selective matching. The selective matching can match the selectively identified points with matching that is appropriate to the local characteristics of the image, which may include region matching, feature matching, feature interpolation, and/or interpolation of previously matched points. For example, regions can be identified in response to the selected points of interest, and the regions may be used to match the selectively identified points of interest. Region matching scores can be determined when the regions are matched, and for regions that are not sufficiently matched, the features of the insufficiently matched regions can be determined and matched to the second image such that these features are used to match the points of interest to the second image. This use of feature matching in response to insufficient region matching provides a more robust match while still providing good matching speed. Soft epi-polar constraints and/or focus constraints can be used to evaluate the matched points of interest, particularly when the surgical field includes interfering objects at different depths from the tissue. Interpolation may be used when confidence scores for feature matching are below a threshold value or bad points are excluded by the constraints.

As an example, the point of interest might be identified with reference to a pixel location of the right image of a tissue. The output of the image matching may generally include the corresponding pixel location of the tissue surface as seen in the left image. Each pixel location effectively provides an associated X-Y location for that eye, with a parallax offset between the coordinate systems generally allowing the depth to be determined per the camera calibration data. The matching may occur while to tool is at the indication location (or if it is in the way, after it moves from between the tissue surface location and camera) and the location marker may snap from the tool to the tissue surface. Alternative location indication techniques and systems might also be employed, such as determining an array of matched tissue surface locations in a region or window around the tool, determining a location of the measurement location on the tool, and snapping the marker to the tissue surface where it is closest to the tool.

Continuing on with exemplary measurement method 110 as shown in FIG. 6, after the first tissue location is designated the system user may then manipulate the master controller to move the tool to the next desired tissue location 122. As the tool moves in the stereoscopic image presented to the system user, a stretch line is superimposed on the image of the site from the prior designated tissue location to the moving measurement tool, and more specifically to the marker which remains superimposed on the measurement tool 124. Increment data may be displayed 126 during movement of the master controller, including the stretch line length, and the like. Optionally, a total length (including prior offsets between pairs of designated tissue locations) may also be superimposed on the image.

When superimposing markers and the like on tissue, on robotic structures (such as tools), or on other structures as shown in the image, it will often be advantageous to have the markers appear at the same depth at which the underlying structure appears in the stereoscopic images presented to the system user. While a variety of methods may be used for matching locations in the left and right images so that the markers appear at the same depth as an underlying tissue or other structure, the particularly efficient and robust image matching technique described in co-pending U.S. Patent Application No. 61/204,082, previously incorporated herein by reference, has significant advantages.

Once the measurement tool has engaged and manipulated (as desired) the next tissue location, the user can actuate the input so as to designate the tissue location 128. Based on data extracted from the image (optionally, also making use of joint-based or kinematic robotic data to verify the image-based location information), the offset data can be updated 130 and another marker superimposed on the designated tissue location 132. In some embodiments, the stretch line may only appear between the immediately prior designated location and the moving tool, while alternative embodiments may fix the stretch line segments so that the user can see the overall contour that has been defined by multiple designated tissue locations. The designated tissue locations may, as mentioned above, be extracted from tool tracking data obtained by image processing of the stereoscopic images presented to the system user, and the data will often include 3-D offsets between tissue locations. The data may define a 3-D polyline that includes a series of straight line segments connecting designated tissue locations so as to define a contour. Alternative embodiments may employ splines or other curving lines between designated points, or they may project the lines onto the underlying or nearest tissue surface as identified by image matching techniques. If the system user indicates this is the last location 134 (and/or the system determines it is the last location such as by effectively enclosing an area, reaching the pre-identified number of line segments of interest, or the like) the final measurement may be displayed 136, with the display often again being superimposed the surgical site. Alternative embodiments may employ display data which is set off from the tissue image, either outside the tissue image window, on a separate display, on a separate window within the tissue image display, or the like. The user may indicate that it is the last location by double clicking the master control handles, depressing the foot pedal, actuating an alternative handle (or both handles), or the like. If the location is not identified as the last location, the system may allow the user to again manipulate the master controller and designate additional tissue locations 122, and so on.

System 50 and method 110 (including variations thereof) can enable accurate in vivo 3-D measurements to be obtained during minimally invasive surgical procedures. These systems and methods can leverage robotic surgical systems that have been developed (including the da Vinci® Surgical System commercially available from Intuitive Surgical, Inc. of California). Alternative embodiments may be based on or added to robotic surgical systems are now being developed or that are developed in the future. The techniques and systems described herein may involve tracking of tools using image data and augmenting the surgical field with graphical information (and particularly with 3-D overlay graphics that depict a measurement cursor or marker, either on a measurement tool or independent of any measurement tool). The measurement location and tool indicators, stretch line and other measurement markers, and output graphics (such as an interactive 3-D numeric readout) can appear on tissue or other structures within the image field, outside the image field but within the surgeon's display, and/or on another auxiliary display system.

In exemplary embodiments, the 3-D overlay visuals may be rendered using a calibrated stereo camera model that is consistent with the surgeon's stereo endoscopic view of the anatomy, so that the 3-D indicator visuals (including points, lines, and/or numerical readouts) are rendered so as to appear coincident in three dimensions with the anatomy or other structures in the field of view. By refreshing the overlay visuals at a sufficient rate, the surgeon may interactively position 3-D markers by effectively steering the markers with the master control input devices 36 on the surgeon's console 16 (see FIG. 2). Moving the tool with the marker allows the surgeon to interact with the tissue when taking measurements, which may avoid placing the marker at a location in space which is inconsistent with the tissue surface, either floating in space above the tissue surface toward the stereoscopic image capture device, or at a location effectively within a tissue surface beyond the tissue location in 3-D space away from the image capture device.

Preferably, the Cartesian position of the instrument tip (or other measurement location) will be determined sufficiently accurately so as to manipulate the 3-D markers for the desired measurement. The Cartesian position will often be determined in the camera reference frame, and the control over the tools provided by the robotic system will facilitate moving the marker in a predictable manner relative to the instrument tip, background tissue and other structures, and the like. To provide the desired accuracy of marker position and movement, image-based tool tracking systems which track the tool position in the camera view can be employed. In alternative embodiments, the robotic manipulator supporting the instrument (optionally the manipulator supporting the camera or other image capture device) may be calibrated (typically prior to initiation of surgery) so as to minimize instrument tip position error in the camera reference frame.

By combining 3-D overlay visuals with accurate information regarding the instruments, a variety of measurement interactions may be achieved. Many of these measurement interactions involve using master-slave following of the instrument tip per movement commands input by the system user to the robotic surgical system. In addition to effecting movement of the tool, movement of a 3-D marker or cursor superimposed on the display of the surgical site, and specifically on the tip of the tool, causes the marker to closely follow the instrument tip. As the instrument tip or distal end of the tool touches anatomy, the 3-D marker will be sufficiently coincident with that anatomy so as to allow accurate location designation. Using a button press or foot switch, the system user samples the current position of the marker and instrument tip. Additional movement of the instrument and button presses may be used to sample a sequence of points. The cumulative Euclidean distance between those sampled points can be interactively computed and displayed to the user. A number of measurement modes may be supported, often using this fundamental instrument measurement interaction. Hence, the surgeon may measure the distance between two or more points in a series. These points may form an open or closed contour. Other quantities may be derived from these points, such as the surface area of a closed contour or the volume of a convex hull of points. The interaction for measuring a long contour may be expedited by automatic sampling of points at regular distance or time intervals, or the like.

In addition to polygon or poly-line representations, spline or similar models can be fit to the data to better approximate the structures of tissue due to its natural tendency towards smoothness. The fitting process can potentially remove some jittering of the hand motion when specifying points. Covariance matrices of a 3-D point can be derived from viewing geometry to account for the non-homogeneity of the error in points (typically resulting in more error in the viewing direction) and may benefit the fitting process.

Points may, in some modes, also be used to efficiently define two-dimensional or 3-D parametric geometric shapes, such as an ellipse, an ellipsoid, soft objects, as used in computer graphics, and the like, optionally using only a few point locations. Properties of the geometric shapes can be derived or determined, such as by calculating the circumference and area of a two-dimensional shape, the volume of a 3-D shape, or the like.

The methods and systems described herein may often be implemented by adding additional software modules to an appropriately equipped robotic surgical system, particularly such a system already having image-based tool tracking capabilities. The virtual measurement software tools described herein may support a variety of modes of interaction between the system and the user, as well as different modes for measurement computation. One such class of interactions between the system user and the computation module may include a single-handed measurement, in which (for example) a single tool is used for measuring the length of a 3-D contour, the surface area of a closed contour, and/or the like. Another type of interaction between the system user and the measurement calculating module may involve the use of two hands and two associated tools, with the tools optionally performing grasping and manipulation during measurements. These measurement tools may generally rely on the ability of a telesurgical system to accurately determine the position of a tool end effector or instrument tip, as well as to accurately highlight or draw on that position in an overlay visual on the display of the system such that it appears coincident with the instrument tip in a 3-D stereoscopic view.

Figure 7:
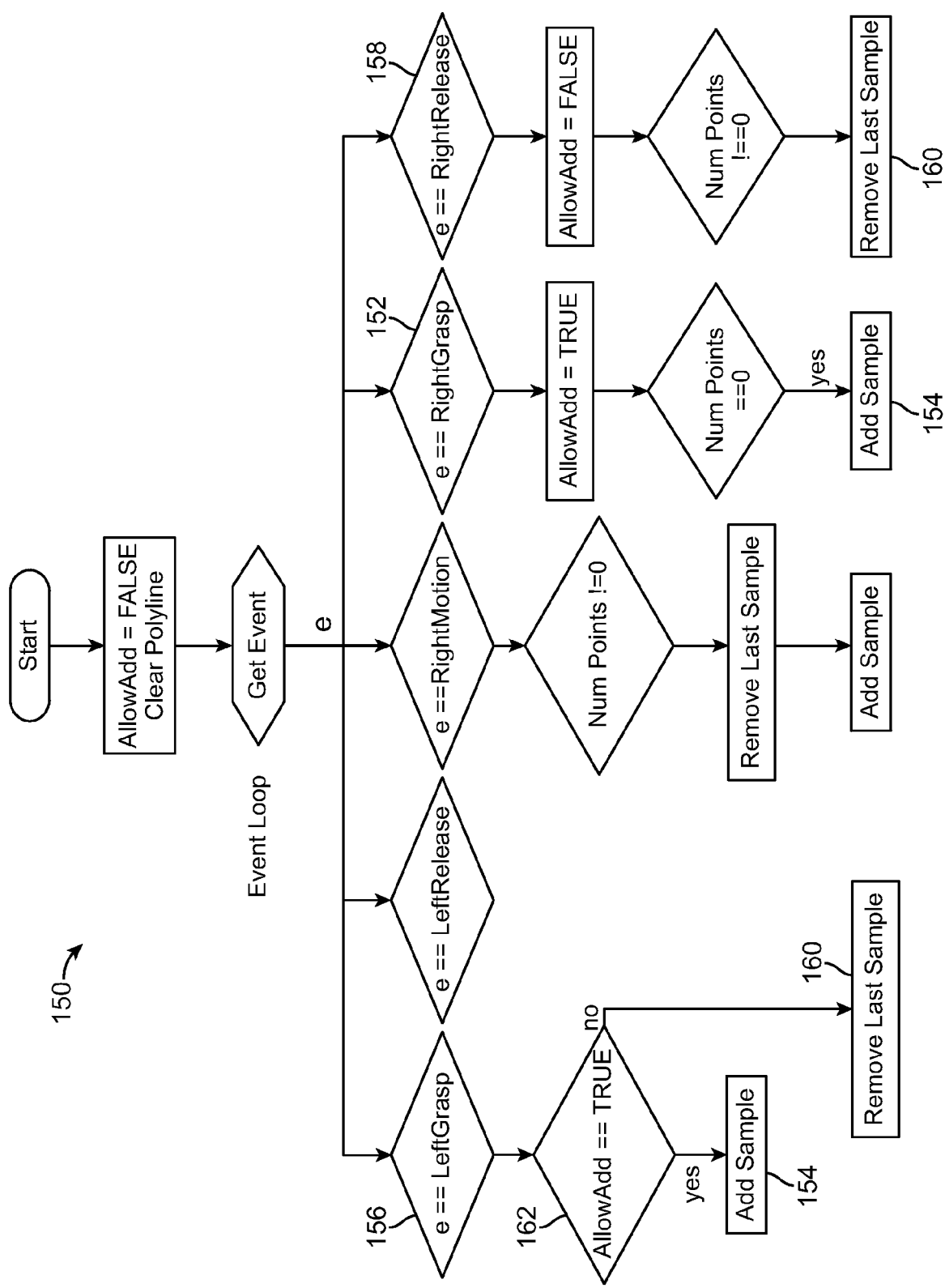
FIG. 7 is a flowchart for contour measurement, and specifically for designating a plurality of tissue or other structure locations.

Referring now to FIG. 7, an exemplary data sampling or designating method 150 may be used for sampling a contour or designating locations. The system user will often use their dominant hand for controlling the measurement instrument tip location, and they may grasp or actuate a handle with their non-dominant hand for adding or removing samples. For example, a right-handed system user will typically use their right hand for steering of the tool and their left hand for designating and/or de-designating locations. For method 150, the right hand is assumed to be the dominant hand and the left hand is assumed to be the non-dominant hand. This may be changed using set up menus, pull down menus, or the like.

Throughout sampling or designation method 150, the right hand may remain in a closed grasp, so that the instrument graspers or jaws remain closed. This may configure a tool having jaws in an advantageous configuration for touching tissue and designating points of interest, and it may optionally identify the measurement tool to the system. The tool jaws are typically closed by closing the paddles of a handle of the master controller. When the right hand grasps the handle 152 the tool is able to add points 154 by briefly grasping with the left hand 156 so as to also close that handle. Using the non-dominant hand for adding and removing points inhibits unintended motion of the dominant hand, which could otherwise adversely affect the accuracy of tool positioning. In alternative embodiments, a foot pedal or additional buttons on the surgeon's console may be provided, preferably such that the input actuation does not interfere with controlled placement of the tool. When the right hand is opened 158, the tool is able to remove points 160 by grasping with the left hand 162.

The system's interaction with the user is such that there is always a point which interactively tracks the instrument tip when in the measurement mode. The system user controls the instrument to position this point to be coincident with the anatomy to be measured. Upon settling on a location, the point may be deposited by grasping with the left hand, which effectively drops the point or point marker at the current location and adds a new point to be interactively moved. To further improve the user interface experience, a poly-line visualization displays a connection between each pair of points in the sequence up to and including the last point at the instrument tip. This provides additional visual confirmation for aligning the direction of the contour relative to the anatomy to be measured. Note that the flow chart of sampling method 150 assumes that 3-D visualization of the measured poly-line is to be redrawn for the operator any time that the poly-line has been changed.

Figure 8:
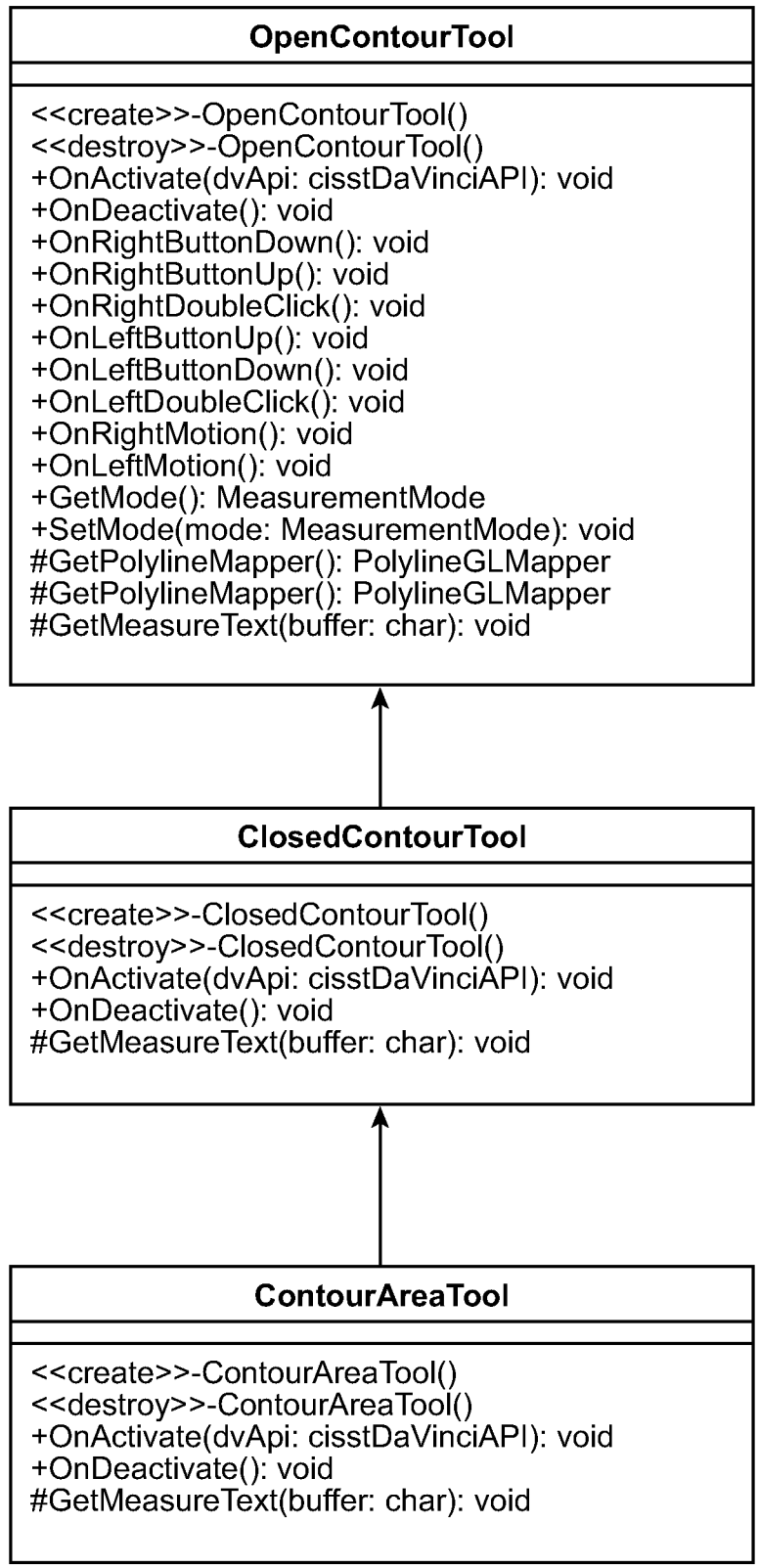
FIG. 8 is a class diagram of contour measurement tools making use of tissue or other structure locations.

Referring now to FIG. 8, a class diagram of the contour-related measurement tools is shown, as well as the inheritance of behavior between those tools. These tools respond to button press events and motion events so as to handle placement of the measured points. The tools support the same point placement interaction modes shown in FIG. 7, but they may differ in the way that they process the series of points to produce measurement text for the display. The supported interaction modes include point-to-point placement for measuring the distance between two points, poly-line point placement for measuring an arbitrary contour, and continuous point placement for producing a spatially regularly sampled measurement.

Figure 9:
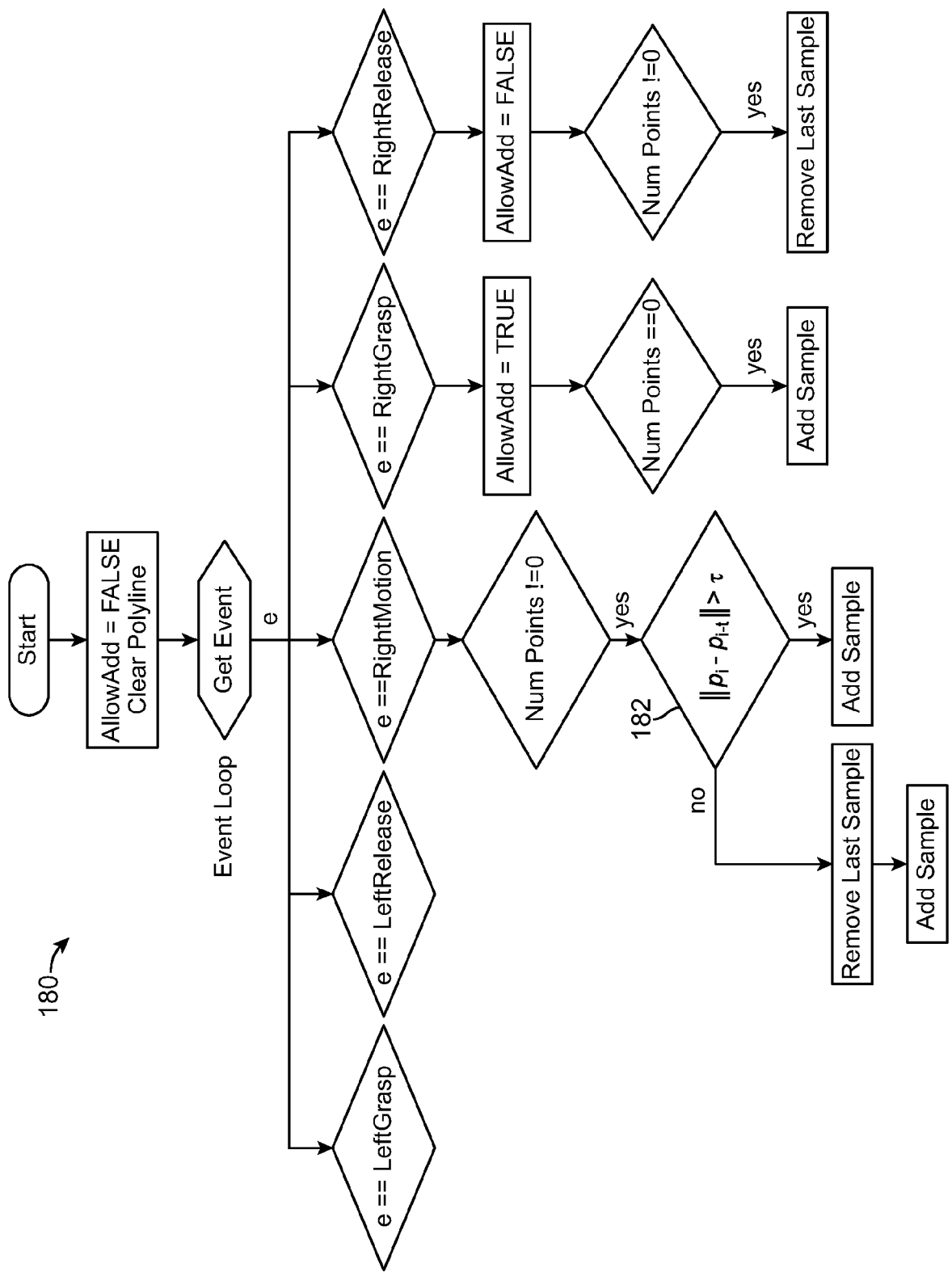
FIG. 9 is a flowchart for an effectively continuous sampling mode to produce regularly spaced locations or samples according to optional embodiments of the invention.

The contour measurement tools also support a continuous sampling mode or location designation method 180, as illustrated in FIG. 9. Method 180 produces regularly spaced samples. The operator may optionally specify a desired sampling tolerance, which determines the minimum spacing between two sample points. A tolerance of between 0.1 millimeter and 20 millimeters may be useful, with a 1 millimeter tolerance often being workable, such that the 1 millimeter tolerance may be used as a default value. Left and right grasping may be used to add or remove points in a manner generally analogous to that described above, with a distance measurement step 182 being used to determine when the tool has been moved sufficiently far so as to justify adding a new sample. Alternative methodologies for sampling may depend on time-based periodic sampling, changes in differential spatial quantities (for example, with samples acquired in response to a continuity and/or curvature of the tool path), or some combined metrics based on spatial and temporal quantities (for example, with samples acquired in response to a velocity and/or acceleration of the tool), or the like.

Referring now to FIGS. 10A and 10B, the contour tools may generally rely on a poly-line 3-D object. This may be used to store a sequence of sampled 3-D points from which to compute length and area measurements. The open contour tool can produce its measurement value using a Compute-Length method of the poly-line 3-D object using the following equation:

$$l = \sum_{2}^{N} \|\rho_i - \rho_{i-1}\|$$ Equation 1

The closed contour tool produces its measurement using Equation 1, and then it adds the length of the segment connecting the last point in the sequence to the first point in the sequence. The closed contour area is computed by approximating the enclosed surface area, optionally using a tessellation of triangles. The area may then be obtained by integrating the area of each triangle. One approach for tessellating the surface is to use a triangle fan with a fixed point at the centroid of the 3-D contour. This works particularly well for convex and nearly convex input, which represents the majority of the contours to be measured.

Embodiments of the invention may also allow a two-handed instrument interaction referred to as hand-over-hand measurement. This can be implemented so as to enable the system user to measure a length of tissue while manipulating the tissue with two grasper instruments, with some or all of the manipulation occurring in the view of the image capture device. For such measurements, a point along the grasper of each tool may be tracked with the Euclidian distance between those points being used to measure the length of tissue currently being grasped. The interaction also allows the system user to sequentially accumulate the length of tissue grasped between the tools. The distance between the tools is automatically sampled and accumulated based on articulation of the tool grasper. Due to the nature of hand-over-hand interactions with the robotic surgical system, one hand can be assumed to be grasping (and thus designating) a new location. Once the new location is grasped and the other hand releases the tissue, the system automatically samples and accumulates the distance between the instruments. This sampling condition is convenient in that it allows the user to grasp and regrasp before committing to the accumulated measurement, such that when a tissue is released from a right-hand tool and the surgeon is reaching along beyond the left-hand tool, the surgeon may move the overall tissue around or move other tissues out of the way before designating the new grasping location by releasing the left-hand tool. Additionally, the system user may have the opportunity to straighten or even slightly stretch the tissue being measured to best approximate the linear segment length that is desired to be sampled.

Figure 11:
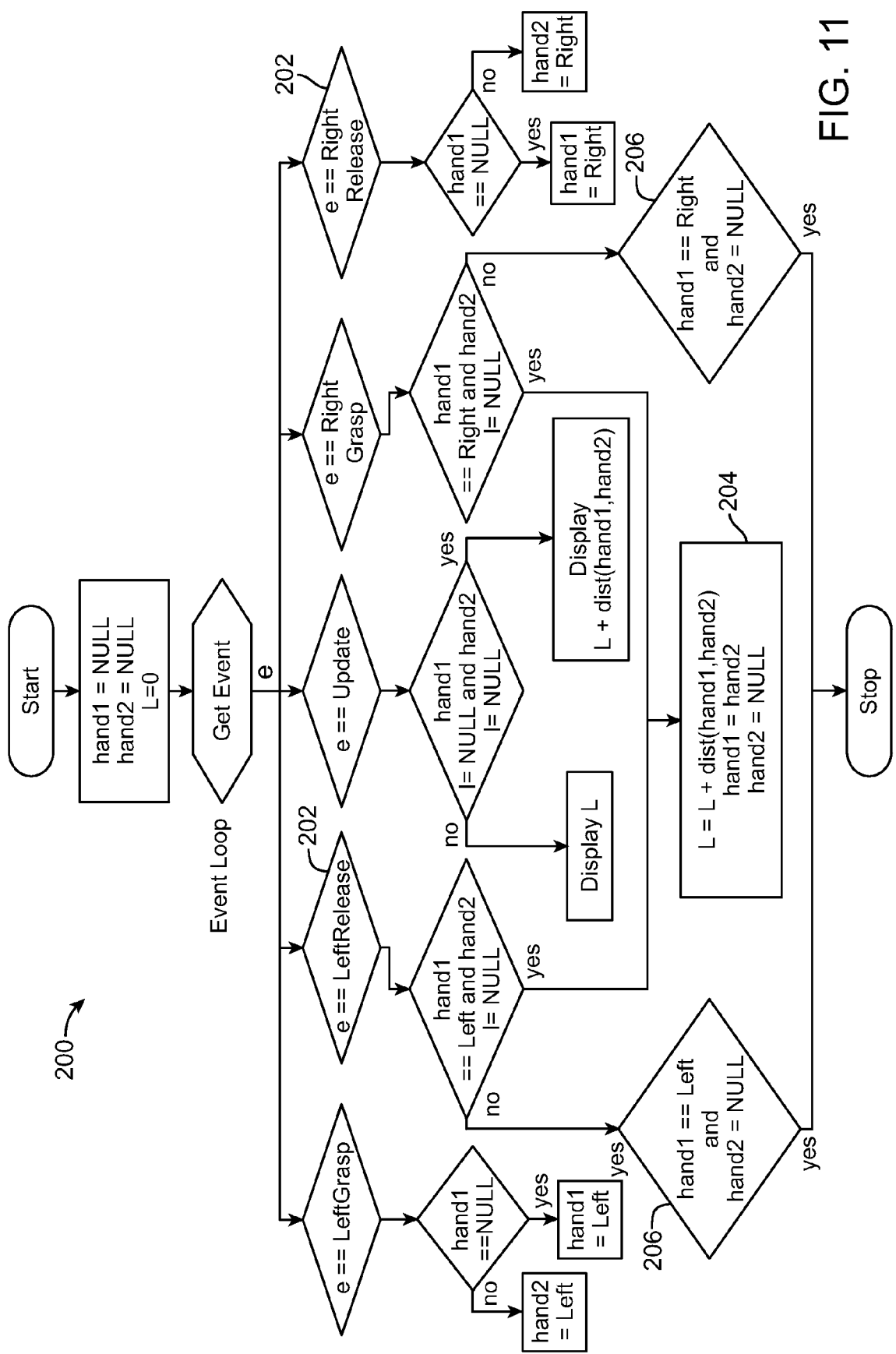
FIG. 11 is a flowchart illustrating software for hand-over-hand tissue or other location designation for measurement.

Referring now to FIG. 11, a hand-over-hand data sampling method 200 allows the user to grasp, manipulate, and move tissue within and/or through the field of view of the image capture device while accumulating a total measured length. The interaction provides an intuitive two-handed measurement paradigm, akin to alternatingly using each hand to pull in a long rope. The interaction does not impose limits on the direction or length of measurement. An operator may measure an arbitrarily long or curvy specimen by making a sequence of piecewise linear measurements. One example use of this measurement interaction is for measuring out a length of bowel in a gastrointestinal procedure. In hand-over-hand sampling method 200, the interaction between the system user and the system has been designed so as to allow the system user to use an alternating pattern of grasping with one hand and measuring with the other hand. The measurement is initiated with the operator grasping the specimen to be measured with one hand or the other. The non-grasping hand becomes the measuring hand. The system continually computes and displays the computed distance between the tools associated with the right and left hands and master command input devices as well as a running total of prior measurements. Before releasing the grasping hand 202, the non-grasping hand is free to grasp and release multiple times before settling on the desired grasp to commit the measured length. Upon releasing the grasping hand 202, the measurement is committed and the relationship between the hands is switched. Committing the measurement involves adding the computed distance between the two tools to a running total 204. The former measuring hand is then left grasping the specimen, and the former grasping hand is now measuring tool free to designate a new location due to the switching of roles 206.

Figure 12:
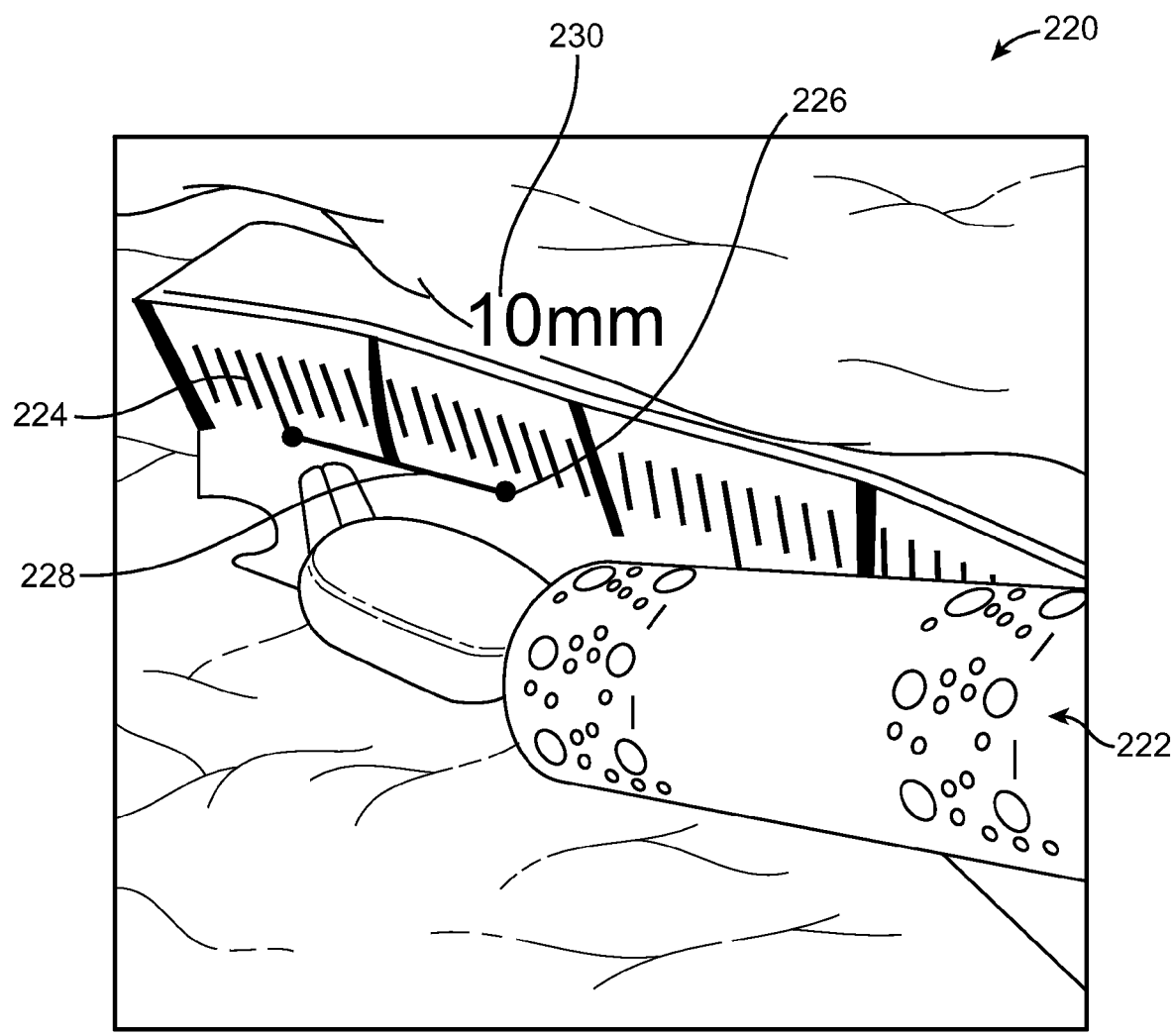
FIG. 12 is a screenshot of a robotic surgical tool image on which designated locations and a stretch line are superimposed.

FIG. 12 is a screen shot graphically showing a point-to-point single line segment measurement using image data. Displayed image 220 shows a tool 222 on which a marker 224 has been superimposed. A marker 226 is shown at a previously designated location, and a stretch line 228 extends between the previously designated location and the marker on the tool. A numerical graphic 230 showing the length of the stretch line is provided offset from the stretch line and within a field of view of the imaging device. Various colors may be used for the displayed stretch line 228 to make it visible against background tissue. In embodiment illustrated by FIG. 12, stretch line 228 is bright green. Likewise, various colors may be used for the displayed markers.

Figure 13:
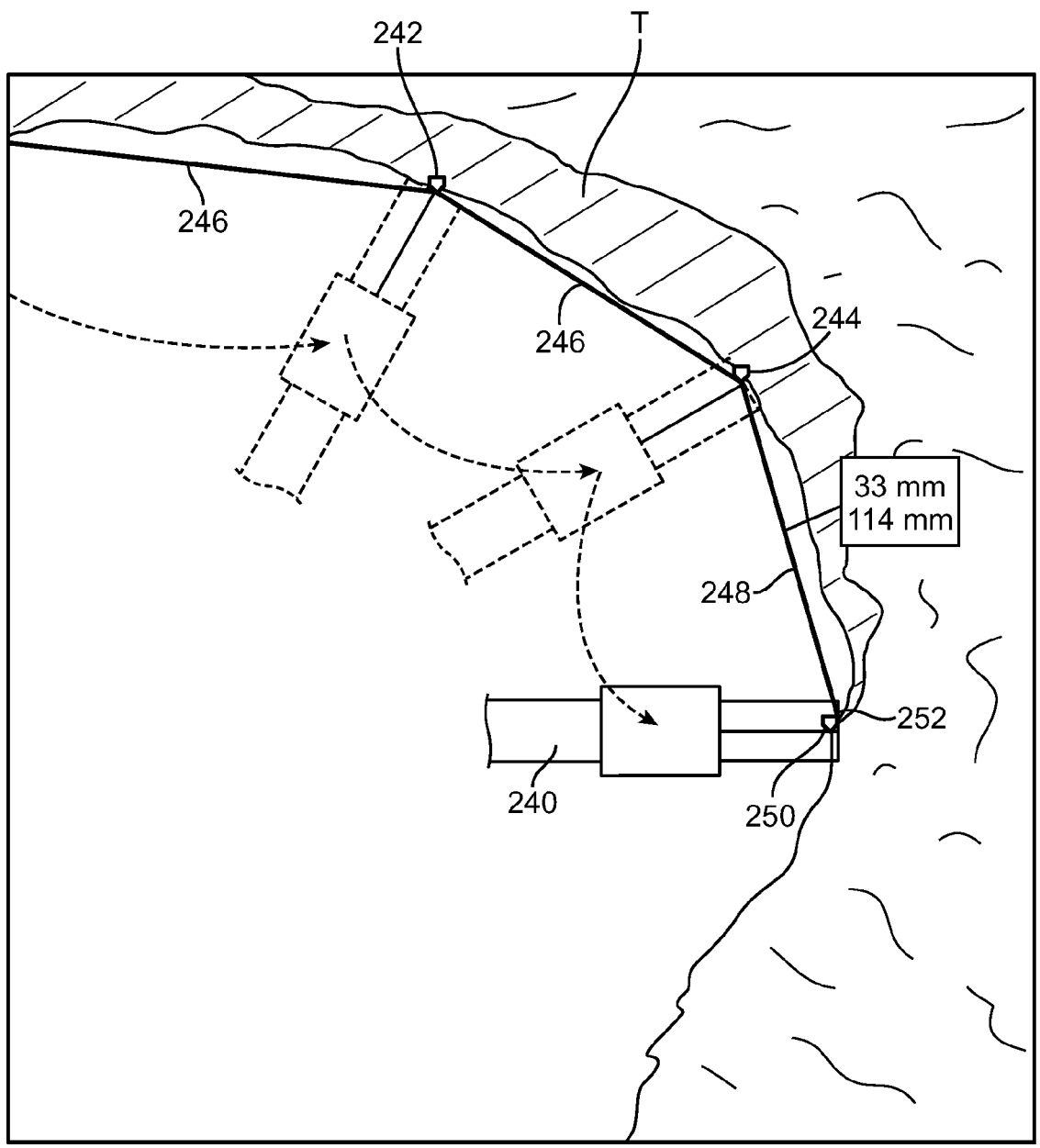
FIG. 13 is a simplified schematic illustration of a single robotic surgical tool designating a contour or continuous series of line segments between tissue locations for cumulative length measurement.

Referring now to FIG. 13, a poly-line measurement is schematically illustrated. A tool 240 has previously been used to designate two tissue locations 242, 244, and displayed markers have been left at those locations after the tool has moved on. Line segments 246 remained fixed between previously designated locations. A stretch line 248 moves with tool 240 and specifically extends between the immediately previously designated location 244 and a measurement location 250 on the tool. A marker 252 is superimposed on the tool at the tool's measurement location so as to appear to move with the tool during measurement. Note that the marked locations need not (and often will not) lie in a line, within a single plane, or the like. Once the tissue locations are designated, the displayed markers may remain with the tissues when the camera moves so as to view an alternate portion of the tissue being measured.

Figure 14:
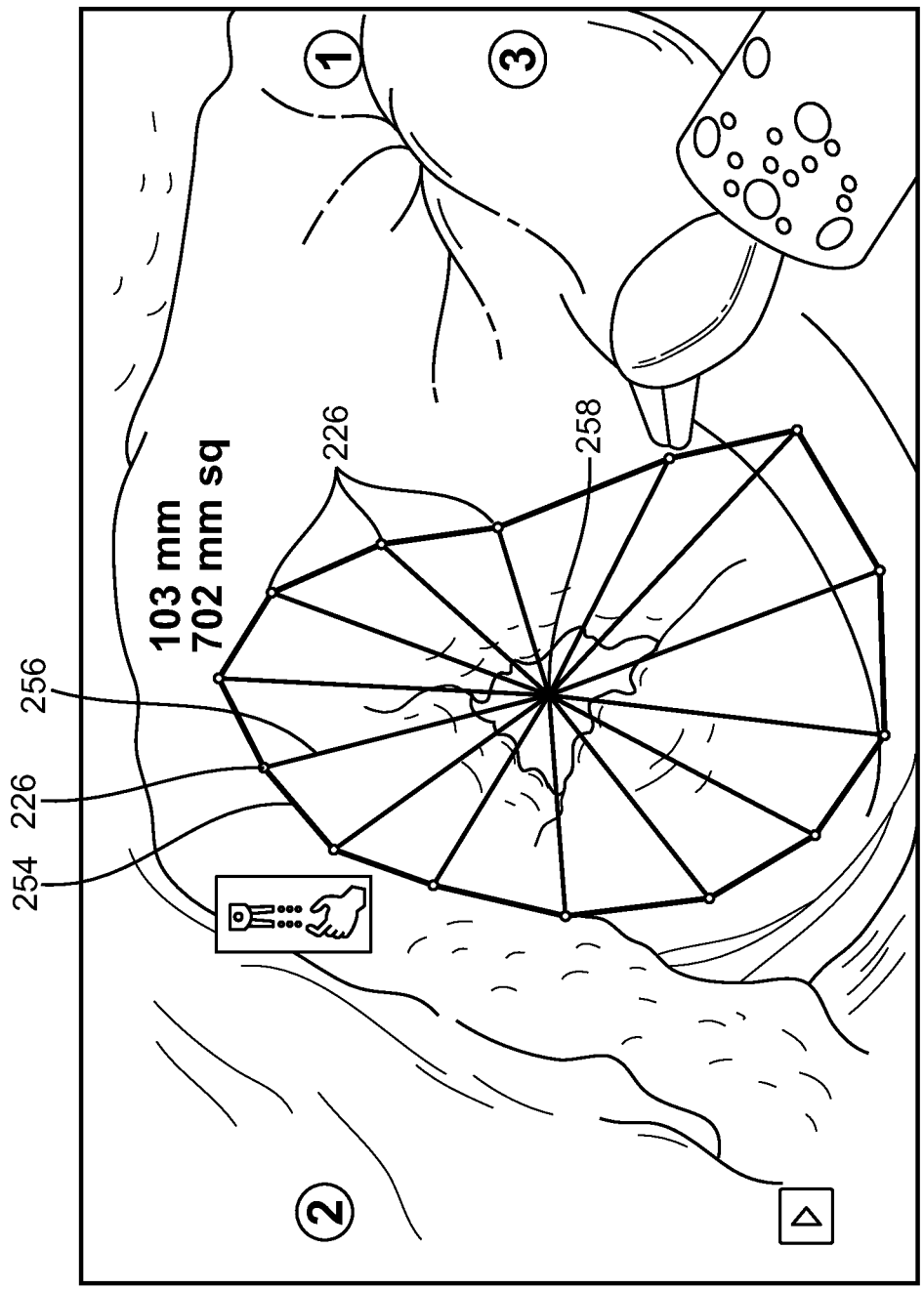
FIG. 14 is a screen shot of a tool being used to measure a circumference and area of a tissue structure.

Referring now to FIG. 14, an exemplary embodiment of an enclosed poly-line measurement can be seen. Note that a circumference and/or area of a tissue structure of interest may be displayed, with the tissue structure here comprising a mitral valve annulus. Differing colors may be used for the different displayed markers or lines. For example, area border lines 254 may be shown in yellow, and tessellation lines 256 extending from a center 258 of the area to each of the displayed markers 226 may be shown in white. The tessellation lines may be used in calculating the area within border lines 254.

Figure 15A:
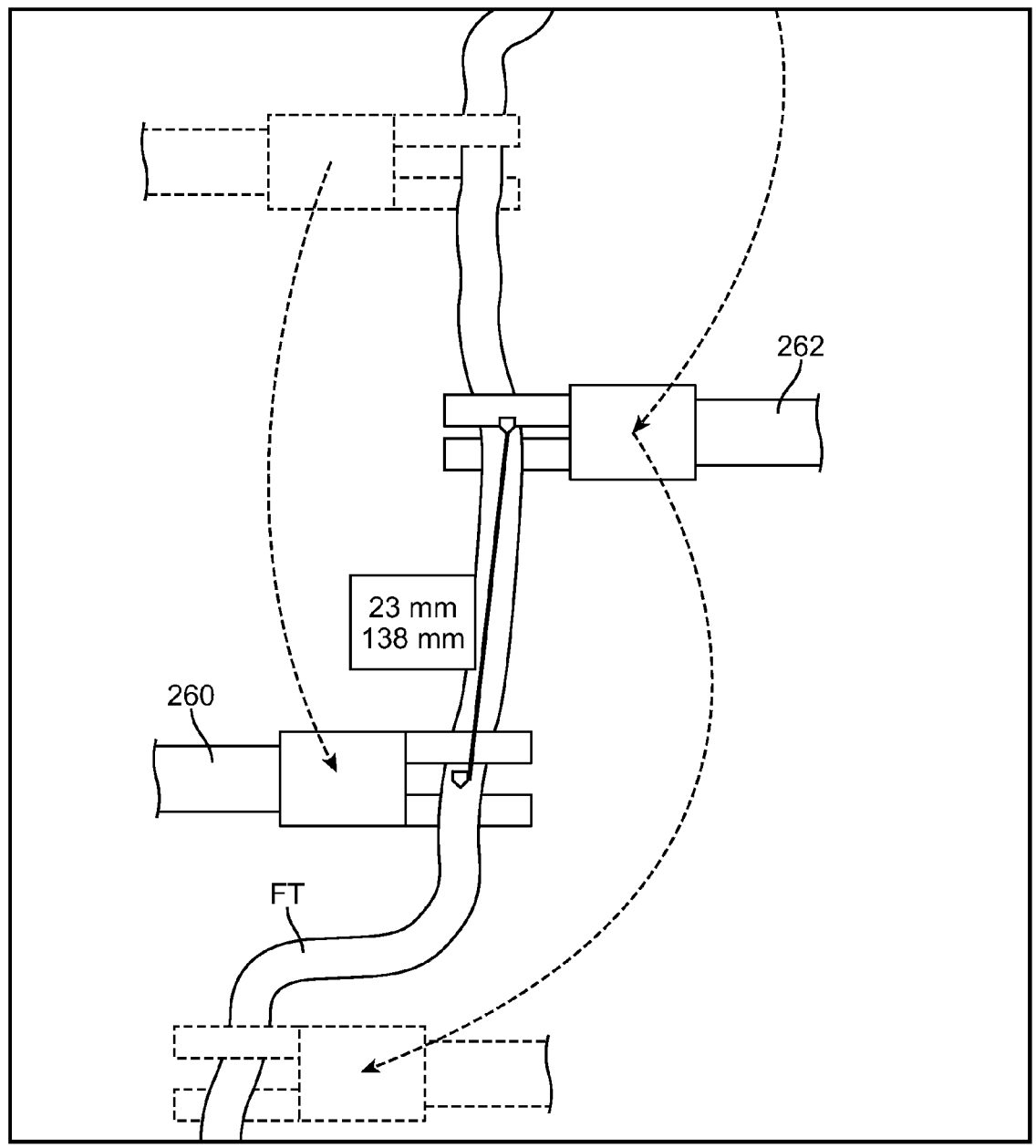
FIG. 15A is a simplified schematic diagram of two surgical robotic tools being used to measure, with a hand-over-hand approach, a length of a flexible tissue structure.
Figure 15B:
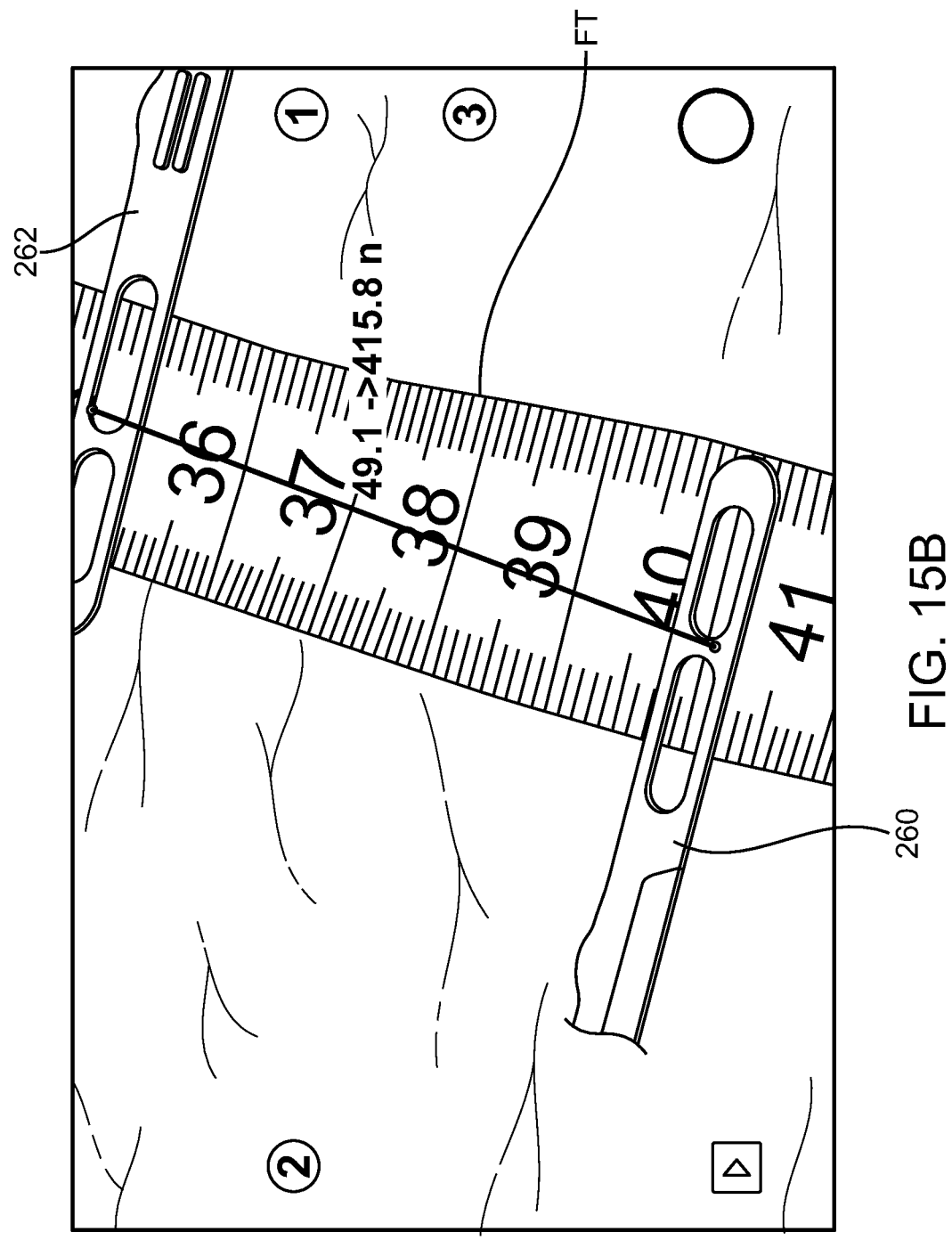
FIG. 15B is a screen shot of two robotic surgical tools obtaining a hand-over-hand measurement.

An exemplary hand-over-hand measurement method can be understood with reference to FIGS. 15A and 15B. Measurement tool 260 moves along flexible tissue or other structure FT (here a measurement tape), generating an output that shows a measurement distance between measurement tool 260 and grasping tool 262. Once the desired location along flexible tissue FT has been identified and the tissue has been appropriately straightened and/or stretched, the measurement tool 260 may remain in a closed grasping mode while grasping tool 262 is released, the action that updates the cumulative distance measurement to include the latest separation between the tools. The separation distance may again be shown with the roles of the two tools switching, with previous measurement tool 260 now being the grasping tool, and so on.

The illustration of FIG. 15B shows verification of hand-over-hand measurement interaction using a tape measure. A line segment is overlaid in three dimensions between the instrument graspers so as to represent the length being measured. A text message is interactively displayed at the mid point of the segment so as to indicate intermediate and cumulative measured lengths.

Additional embodiments may combine a number of the techniques and systems described above with a still stereoscopic image so as to facilitate measurements of offsets, areas, volumes, aspect ratios, and the like. For example, it may be desirable to obtain measurements from moving tissues, particularly for measurements of tissue structures of the heart during closed-chest beating heart procedures. So as to facilitate accurate measurements during such physiological movement, the processor can freeze the stereo video images presented to a system user (such as the stereoscopic image presented to one or more surgeon in the surgeon's console, or the two dimensional image presented to an assistant or proctor in an associated display). The image may be frozen per an input from a system user in preparation for designating tissue locations, or in response to an input indicating that the robotic tool is disposed at or adjacent a first tissue location. Regardless, the same (or a different) system user can then identify one or more tissue locations in the frozen image. Optionally, tissue locations can by identified by using a master input device of the surgeon's console to steer a 3d cursor to the desired location of the tissue image. Alternatively, the systems user may simply designate a location in one of the two frozen stereoscopic images. In either case, the cursor may snap to the tissue surface based on a location of the cursor in one of the stereoscopic images when a tissue designation command is received by the processor. When the desired tissue locations have been entered in the frozen image, three dimensional offsets and measurements may be determined from the three dimensional image data as described above. While all of the tissue locations may optionally be indicated using a cursor or the like, indication of at least the first location with a robotic tool may help to stabilize the local tissue. For measurements of a beating heart and/or other cyclically moving tissues, a time series images may be captured and used to generate a sequence of measurements at different stages of a tissue movement cycle. Hence, such systems and methods can (for example) capture a series of cyclic pumping states of the heart and perform measurements of those states to enhance diagnosis and treatment of a variety of heart conditions.

While exemplary embodiments have been described in some detail for clarity of understanding and by way of example, a variety of modifications, adaptations, and changes will be obvious to those of skill in the art. Hence, the scope of the present invention is limited solely by the appended claims.

What is claimed is:

1. A method for measuring a length along a tissue structure, the method comprising: grasping a first three-dimensional (3-D) location on the tissue structure with a first grasping tool in response to a first command received at a first input command device operatively coupled using one or more processors to the first grasping tool so as to allow a system user to manipulate the first grasping tool control console; grasping a second 3-D location on the tissue structure with a second grasping tool in response to a second command received at a second input command device operatively coupled using the one or more processors to the second grasping tool so as to allow a system user to manipulate the second grasping tool; configuring the one or more processors to measure, using the one or more processors, three dimensional distances between grasped locations of the tissue structure during hand-over-hand sampling; with the one or more processors, measuring a first three dimensional distance between the first 3-D location and the second 3-D location so as to provide a first three dimensional distance measurement; releasing the first grasping tool from grasping the first 3-D location and then grasping a third 3-D location on the tissue structure with the first grasping tool in response to a third command received at the first input command device, the first, second, and third 3-D locations being in sequence along the tissue structure; with the one or more processors, measuring a second three dimensional distance between the second 3-D location and the third 3-D location so as to provide a second three dimensional distance measurement; and with the one or more processors, outputting a sum of the measured first and second three dimensional distances; wherein the tissue structure comprises a tissue structure within a minimally invasive surgical site; and further comprising: grasping a sequence of additional tissue structure locations by alternately moving the first and second grasping tools and grasping the tissue structure alternatingly with the first and second grasping tools in response to commands received at the first and second input command devices; configuring the one or more processors to process stereoscopic image data; and with the one or more processors, receiving stereoscopic image data comprising left and right stereoscopic images of the tissue structure and of the first and second grasping tools from an image capture device and outputting to a display an image of the tissue structure and of the first and second grasping tools; wherein the image is outputted in real time in the course of movement of the first and second grasping tools; and wherein the image includes an image of a stretch line that is superimposed on the image of the tissue structure from a prior grasped tissue location to a currently grasping grasping tool.

2. The method of claim 1, wherein the first 3-D location, the second 3-D location, and the third 3-D location are 3-D tissue locations along the tissue structure, and wherein the 3-D tissue locations are designated by actuation of the grasping tools in response to commands received at the first and second input command devices.

3. The method of claim 2, wherein releasing of the first grasping tool from the first 3-D tissue location while the second grasping tool grasps the second 3-D tissue location designates the second 3-D tissue location, and wherein the designation of the 3-D second tissue location initiates the first three dimensional distance measurement between the first 3-D location and the second 3-D) location.

4. The method of claim 3, wherein releasing of the second grasping tool from the second 3-D tissue location in response to commands received at the second input command device while the first grasping tool grasps the third 3-D tissue location designates the third 3-D tissue location, and wherein the designation of the third 3-D tissue location initiates the second three dimensional distance measurement between the second location and the third location.

5. The method of claim 1, further comprising: with the one or more processors, outputting to a display, an image capture device field of view including the tissue structure, wherein the third location is not visible in the field of view while measuring the first three dimensional distance between the first location and the second location, and manipulating the tissue structure with the grasping tools or moving the field of view in response to commands received at the first and second input command devices so as to output an image of the third location while measuring the second three dimensional distance between the second location and the third location.

6. The method of claim 1, further comprising with the one or more processors, receiving image data comprising left and right stereoscopic images of the tissue structure from an image capture device, wherein the three dimensional distances are measured by determining three dimensional distances between the first and second locations and the second and third locations using the image data.

7. The method of claim 1, wherein the image includes an image of a stretch line that is superimposed on the image of the tissue structure between the currently grasping tool and a currently moving measurement grasping tool.

8. A method for measuring a length along a tissue structure, the method comprising: grasping a first three-dimensional (3-D) location on the tissue structure with a first tool in response to a first command received at a first input command device operatively coupled using one or more processors to the first grasping tool so as to allow a system user to manipulate the first grasping tool control console; grasping a second 3-D location on the tissue structure with a second tool in response to a second command received at a second input command device operatively coupled using the one or more processors to the second grasping tool so as to allow a system user to manipulate the second grasping tool; configuring the one or more processors to measure, using the one or more processors, three dimensional distances between grasped locations of the tissue structure during hand-over-hand sampling; with the one or more processors, measuring a first three dimensional distance between the first 3-D location and the second 3-D location so as to provide a first three dimensional distance measurement; releasing the first grasping tool from grasping the first 3-D location and then grasping a third 3-D location on the tissue structure with the first grasping tool in response to a third command received at the first input command device, the first, second, and third 3-D locations being in sequence along the tissue structure; with the one or more processors, measuring a second three dimensional distance between the second 3-D location and the third 3-D location so as to provide a second three dimensional distance measurement; and with the one or more processors, outputting a sum of the measured first and second three dimensional distances; wherein the tissue structure comprises a tissue structure within a minimally invasive surgical site, and further comprising: grasping a sequence a plurality of additional tissue structure locations by alternately moving the first and second grasping tools and grasping the tissue structure alternatingly with the first and second grasping tools in response to commands received at the first and second input command devices; with the one or more processors, measuring a sequence of additional three dimensional distances between a sequence of additional tissue structure 3-D locations so as to provide a sequence of additional three dimensional distance measurements; wherein the three dimensional distances are each defined by a pair of the locations; and further comprising: configuring the one or more processors to process stereoscopic image data, with the one or more processors, during the acts of grasping and releasing with the first and second grasping tools and measuring three-dimensional distances, outputting to a display in real time in the course of movement of the first and second grasping tools: a) a graphical indicator of a measurement location along each grasping tool, b) a stretch line between a measurement location indicated by the graphical indicator along the first grasping tool and a measurement location indicated by the graphical indicator along the second grasping tool, c) a distance measurement between the first and second grasping tools, and d) a current cumulative measurement including the sum of distance measurements for one or more of the additional three dimensional distances, wherein each of a)-d) is superimposed on an image of the minimally invasive surgical site.

9. A method for measuring a length along a tissue structure, the method comprising: grasping a first three-dimensional (3-D) location on the tissue structure with a first tool in response to a first command received at a first input command device operatively coupled using one or more processors to the first grasping tool so as to allow a system user to manipulate the first grasping tool control console; grasping a second 3-D location on the tissue structure with a second tool in response to a second command received at a second input command device operatively coupled using the one or more processors to the second grasping tool so as to allow a system user to manipulate the second grasping tool; configuring the one or more processors to measure, using the one or more processors, three dimensional distances between grasped locations of the tissue structure during hand-over-hand sampling; with the one or more processors, measuring a first three dimensional distance between the first 3-D location and the second 3-D location so as to provide a first three dimensional distance measurement; releasing the first grasping tool from grasping the first 3-D location and then grasping a third 3-D location on the tissue structure with the first grasping tool in response to a third command received at the first input command device, the first, second, and third 3-D locations being in sequence along the tissue structure; with the one or more processors, measuring a second three dimensional distance between the second 3-D location and the third 3-D location so as to provide a second three dimensional distance measurement; and with the one or more processors, outputting a sum of the measured first and second three dimensional distances; with the one or more processors, receiving stereoscopic image data comprising left and right stereoscopic images of the tissue structure and of the first and second grasping tools from an image capture device and outputting to a display an image of the tissue structure and of the first and second grasping tools and of a representation of the measured first and second three dimensional distances; wherein the image is outputted in real time in the course of movement of the first and second grasping tools; wherein the tissue structure comprises a tissue structure within a minimally invasive surgical site, and further comprising: grasping a sequence a plurality of additional tissue structure locations by grasping the tissue structure alternatingly with the first and second grasping tools in response to commands received at the first and second input command devices; wherein the first 3-D location, the second 3-D location, and the third 3-D location are 3-D tissue locations along the tissue structure; wherein the 3-D tissue locations are designated by actuation of the grasping tools in response to commands received at the first and second input command devices; and wherein while the first tool remains grasped, the second tool is allowed to grasp and release multiple times in response to commands received at the first input command device until a desired tissue location is achieved; wherein a three dimensional distance measurement between the plurality of additional locations is measured by releasing the first tool in response to commands received at the first input command device while the second grasping tool grasps the desired tissue location; and wherein location designation responsibility between the first grasping tool and the second grasping tool switches when the first grasping tool is released.

10. A method for measuring a length along a tissue structure, the method comprising: grasping a first three-dimensional (3-D) location on the tissue structure with a first tool in response to a first command received at a first input command device operatively coupled using one or more processors to the first grasping tool so as to allow a system user to manipulate the first grasping tool control console; grasping a second 3-D location on the tissue structure with a second tool in response to a second command received at a second input command device operatively coupled using the one or more processors to the second grasping tool so as to allow a system user to manipulate the second grasping tool; configuring the one or more processors to measure, using the one or more processors, three dimensional distances between grasped locations of the tissue structure during hand-over-hand sampling; with the one or more processors, measuring a first three dimensional distance between the first 3-D location and the second 3-D location so as to provide a first three dimensional distance measurement; releasing the first grasping tool from grasping the first 3-D location and then grasping a third 3-D location on the tissue structure with the first grasping tool in response to a third command received at the first input command device, the first, second, and third 3-D locations being in sequence along the tissue structure; with the one or more processors, measuring a second three dimensional distance between the second 3-D location and the third 3-D location so as to provide a second three dimensional distance measurement; and with the one or more processors, outputting a sum of the measured first and second three dimensional distances; with the one or more processors, receiving stereoscopic image data comprising left and right stereoscopic images of the tissue structure and of the first and second grasping tools from an image capture device and outputting to a display an image of the tissue structure and of the first and second grasping tools and of a representation of the measured first and second three dimensional distances; wherein the image is outputted in real time in the course of movement of the first and second grasping tools; wherein the tissue structure comprises a tissue structure within a minimally invasive surgical site, and further comprising: grasping a sequence a plurality of additional tissue structure locations by grasping the tissue structure alternatingly with the first and second grasping tools in response to commands received at first and second input command devices; further comprising: manipulating the tissue structure with the grasping tools in response to commands received at the first and second input command devices so as to straighten or stretch a length of the tissue structure when an associated three dimensional distance between the first and second grasping tools is measured.

11. A system to measure a length along a tissue structure, the system comprising: a manipulator coupled using one or more processors to manipulate a first grasping tool in response to movement commands and coupled using the one or more processors to manipulate a second grasping tool in response to movement commands; the one or more processors are configured to: receive a first command to grasp a first 3-D location on the tissue structure with the first grasping tool and in response to receiving the first command, to determine and transmit an associated first instruction to a manipulator system coupled with the first grasping tool; receive a second command to grasp a second 3-D location on the tissue structure with the second grasping tool and in response to receiving the second command, to determine and transmit an associated second instruction to the manipulator system coupled with the second grasping tool; measure, using the one or more processors, a first three dimensional distance between the first 3-D location and the second 3-D location so as to provide a first three dimensional distance measurement; and couple the grasping tools to an output such that an input command from a user induces the one or more processors to sum three-dimensional distances between the 3-D locations so as to measure a hand-over-hand length along the tissue structure; wherein the one or more processors designates the second 3-D tissue location, currently grasped by the second grasping tool as a grasping location, in response to commands to release jaws of the first grasping tool from the first 3-D location; and wherein the one or more processors adds the first three dimensional distance measurement between the first 3-D location and the second 3-D location to the hand-over-hand length after designating the second tissue 3-D location as the grasping location so that the first grasping tool may be commanded to grasp and release a plurality of candidate third tissue 3-D locations without altering the hand-over-hand length; and the one or more processors configured to receive stereoscopic image data comprising left and right stereoscopic images of the tissue structure and of the first and second grasping tools from an image capture device and outputting to a display an image of the tissue structure and of the first and second grasping tools and of a representation of the measured first and second three dimensional distances; wherein the image is outputted in real time in the course of movement of the first and second grasping tools.

12. A system to measure a length along a structure, the system comprising: a manipulator coupled using one or more processors to manipulate a first grasping tool in response to movement commands and coupled using the one or more processors to manipulate a second grasping tool in response to movement commands; the one or more processors configured to: receive a first command to grasp a first 3-D location on the tissue structure with the first grasping tool and in response to receiving the first command, to determine and transmit an associated first instruction to a manipulator system coupled with the first grasping tool; receive a second command to grasp a second 3-D location on the tissue structure with the second grasping tool and in response to receiving the second command, to determine and transmit an associated second instruction to the manipulator system coupled with the second grasping tool; measure, using the one or more processors, a first three dimensional distance between the first 3-D location and the second 3-D location so as to provide a first three dimensional distance measurement; and couple the grasping tools to an output such that an input command from a user induces the one or more processors to sum three dimensional distances between the 3-D locations so as to measure a hand-over-hand length along the tissue structure; wherein the one or more processors is configured to defer a summation of three dimensional distances until a 3-D location is indicated per a command from the user so as to manipulate the tissue structure with the grasping tools during measurement of the hand-over-hand length and allow the grasping tools to straighten or stretch a measured length of the tissue structure when an associated distance between the first and second grasping tools is measured; and the one or more processors configured to receive stereoscopic image data comprising left and right stereoscopic images of the tissue structure and of the first and second grasping tools from an image capture device and outputting to a display an image of the tissue structure and of the first and second grasping tools and of a representation of the measured first and second three dimensional distances; wherein the image is outputted in real time in the course of movement of the first and second grasping tools.

13. A system to measure a length along a structure, the system comprising: a manipulator coupled using one or more processors to manipulate a first grasping tool in response to movement commands and coupled using the one or more processors to manipulate a second grasping tool in response to movement commands; the one or more processors configured to: receive a first command to grasp a first 3-D location on the tissue structure with the first grasping tool and in response to receiving the first command, to determine and transmit an associated first instruction to a manipulator system coupled with the first grasping tool; receive a second command to grasp a second 3-D location on the tissue structure with the second grasping tool and in response to receiving the second command, to determine and transmit an associated second instruction to the manipulator system coupled with the second grasping tool; measure, using the one or more processors, a first three dimensional distance between the first 3-D location and the second 3-D location so as to provide a first three dimensional distance measurement; and couple the grasping tools to an output such that an input command from a user induces the processor to sum three dimensional distances between the 3-D locations so as to measure a hand-over-hand length along the tissue structure; wherein the one or more processors is further configured to output an image capture device field of view to a display; wherein the one or more processors is configured to receive and execute commands for articulation of the tools to grasp and manipulate the structure so as to bring a third 3-D location on the tissue structure into the field of view, and after the third 3-D location on the structure is in the field of view, to determine a distance between the second 3-D location and the third 3-D location; and the one or more processors configured to receive stereoscopic image data comprising left and right stereoscopic images of the tissue structure and of the first and second grasping tools from an image capture device and outputting to a display an image of the tissue structure and of the first and second grasping tools and of a representation of the measured first and second three dimensional distances; wherein the image is outputted in real time in the course of movement of the first and second grasping tools.

14. A system to measure a length along a structure, the system comprising: a manipulator coupled using one or more processors to manipulate a first grasping tool in response to movement commands and coupled using the one or more processors to manipulate a second grasping tool in response to movement commands; the one or more processors configured to: receive a first command to grasp a first 3-D location on the tissue structure with the first grasping tool and in response to receiving the first command, to determine and transmit an associated first instruction to a manipulator system coupled with the first grasping tool; receive a second command to grasp a second 3-D location on the tissue structure with the second grasping tool and in response to receiving the second command, to determine and transmit an associated second instruction to the manipulator system coupled with the second grasping tool; measure, using the one or more processors, a first three dimensional distance between the first 3-D location and the second 3-D location so as to provide a first three dimensional distance measurement; and couple the grasping tools to an output such that an input command from a user induces the one or more processors to sum three dimensional distances between the 3-D locations so as to measure a hand-over-hand length along the tissue structure; wherein the one or more processors is configured to determine and transmit instructions to the manipulator system to grasp and release multiple times using the second grasping tool, in response to received commands, until a desired tissue 3-D location is achieved; wherein a distance measurement between the additional 3-D locations is measured in response to release of the first grasping tool while the second tool grasps the desired 3-D tissue location; and wherein 3-D location designation responsibility between the first grasping tool and the second grasping tool switches in response to release of the first grasping tool, and the one or more processors configured to receive stereoscopic image data comprising left and right stereoscopic images of the tissue structure and of the first and second grasping tools from an image capture device and outputting to a display an image of the tissue structure and of the first and second grasping tools and of a representation of the measured first and second three dimensional distances; wherein the image is outputted in real time in the course of movement of the first and second grasping tools.

* * * * *